United States Patent
Yamagishi et al.

(10) Patent No.: US 12,161,414 B2
(45) Date of Patent: Dec. 10, 2024

(54) REFLECTIVITY JUDGEMENT APPARATUS, REFLECTIVITY JUDGEMENT METHOD, AND PROGRAM

(71) Applicant: NIPPON TELEGRAPH AND TELEPHONE CORPORATION, Tokyo (JP)

(72) Inventors: Shimpei Yamagishi, Tokyo (JP); Makoto Yoneya, Tokyo (JP); Shigeto Furukawa, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 1017 days.

(21) Appl. No.: 17/255,499

(22) PCT Filed: May 20, 2019

(86) PCT No.: PCT/JP2019/019836
§ 371 (c)(1),
(2) Date: Dec. 23, 2020

(87) PCT Pub. No.: WO2020/003804
PCT Pub. Date: Jan. 2, 2020

(65) Prior Publication Data
US 2021/0275016 A1 Sep. 9, 2021

(30) Foreign Application Priority Data
Jun. 25, 2018 (JP) .................. 2018-119437

(51) Int. Cl.
*A61B 3/113* (2006.01)
*A61B 3/00* (2006.01)
(Continued)

(52) U.S. Cl.
CPC ............ *A61B 3/113* (2013.01); *A61B 3/0091* (2013.01); *A61B 5/163* (2017.08); *G06T 7/246* (2017.01);
(Continued)

(58) Field of Classification Search
CPC ....... A61B 5/163; A61B 3/0091; A61B 3/113; A61B 5/162; G02B 2027/0138;
(Continued)

(56) References Cited

U.S. PATENT DOCUMENTS

2003/0025652 A1* 2/2003 Susnfara ................ G06T 15/20
345/8
2014/0249447 A1 9/2014 Sereno et al.
(Continued)

FOREIGN PATENT DOCUMENTS

| JP | 2015-132782 A | 7/2015 |
| JP | 2016-151849 A | 8/2016 |
| JP | 2017-215963 A | 12/2017 |

*Primary Examiner* — David J. McCrosky

(57) ABSTRACT

The present invention provides a technique for judging the reflexivity of an eyeball movement. The judging the reflexivity comprises extracting a first feature value of a saccade appearing in a pupil movement performed by a subject during a task involving moving an eye so as to follow a visual cue and a second feature value of a saccade during a task involving moving the eye in an opposite direction to the visual cue. A judgement result indicates whether an eyeball movement performed by the subject has occurred reflexively based on a degree of difference between the first feature value and the second feature value. The judging further comprises generating, based on the degree of difference between the first and second feature values, a judgement result indicating whether the eyeball movement performed by the subject has occurred reflexively.

12 Claims, 10 Drawing Sheets

(51) Int. Cl.
*A61B 5/16* (2006.01)
*G06T 7/246* (2017.01)

(52) U.S. Cl.
CPC ............... *G06T 2207/10048* (2013.01); *G06T 2207/30041* (2013.01)

(58) Field of Classification Search
CPC ...... G02B 2027/014; G02B 2027/0178; G02B 27/017; G02B 27/0172; G06F 3/013; G06F 3/012; G06F 3/0304; G06T 2207/30041
See application file for complete search history.

(56) References Cited

U.S. PATENT DOCUMENTS

| | | |
|---|---|---|
| 2016/0062459 A1 | 3/2016 | Publicover et al. |
| 2016/0128558 A1* | 5/2016 | Larin .................. A61B 3/0025 600/407 |

* cited by examiner

REFLECTIVITY JUDGEMENT APPARATUS, REFLECTIVITY JUDGEMENT METHOD, AND PROGRAM

CROSS-REFERENCE TO RELATED APPLICATIONS

This application is a U.S. 371 Application of International Patent Application No. PCT/JP2019/019836, filed on 20 May 2019, which application claims priority to and the benefit of JP Application No. 2018-119437, filed on 25 Jun. 2018, the disclosures of which are hereby incorporated herein by reference in their entireties.

TECHNICAL FIELD

The present invention relates to a technique for judging whether or not an eyeball movement is reflexive.

BACKGROUND ART

In a well-known, conventional technique, a determination as to whether or not a sound is a noticeable sound (a highly perceptible sound) is made on the basis of a feature value relating to a saccade of the eye of a person who is in a state of being able to hear the sound (PTL 1). In this technique, a determination as to whether or not a presented sound is a noticeable sound is made on the basis of a degree of difference between a feature value of a saccade performed when the sound is presented and a feature value of a saccade performed when the sound is not presented.

CITATION LIST

Patent Literature

[PTL 1] Japanese Patent Application Publication No. 2015-132782

SUMMARY OF THE INVENTION

Technical Problem

In PTL 1, noticeable sounds include not only sounds that can be heard unexpectedly without paying attention (sounds that attract attention), but also sounds that can be heard when listening carefully, and it is therefore impossible to determine whether the movement of the eyeball occurred unconsciously (reflexively) in response to an external stimulus, or consciously. In other words, it is impossible to determine, with respect to the reflexivity of the eyeball movement, whether or not the eyeball movement was a reflexive movement caused by an external stimulus and so on.

Hence, an object of the present invention is to provide a technique for judging the reflexivity of an eyeball movement.

Means for Solving the Problem

A reflexivity judgement apparatus of the present invention includes a feature value extraction unit and a judgement unit. The judgement unit uses a feature value of a saccade appearing in an eyeball movement by the subject, the feature value having been extracted by the feature value extraction unit, to generate a judgement result indicating a reflexivity of the eyeball movement by the subject or a reflexivity relating to the eye of the subject.

Effects of the Invention

According to the present invention, the reflexivity of an eyeball movement can be judged.

DESCRIPTION OF EMBODIMENTS

Embodiments of the present invention will be described in detail below. Note that constituent parts having identical functions have been allocated identical numerals, and duplicate description thereof has been omitted.

TECHNICAL BACKGROUND

The respective embodiments of the present invention are based on the discovery of a natural law according to which there is a difference between a feature value of a saccade performed when the eye moves reflexively in response to an external stimulus and a feature value of a saccade performed when the eye is moved consciously so as to suppress reflexivity, and in the respective embodiments of the present invention, this discovery is used to judge the reflexivity of an eyeball movement.

First, tests that serves as a basis and results thereof will be described below.
[Test 1]
(1) Task 1A
An image of a focus point serving as a visual cue is displayed on a display placed in front of a subject, and after a fixed period of time, the position of the focus point is moved left or right, the subject being instructed to move his/her eyes so as to follow the focus point.

Figure 1:
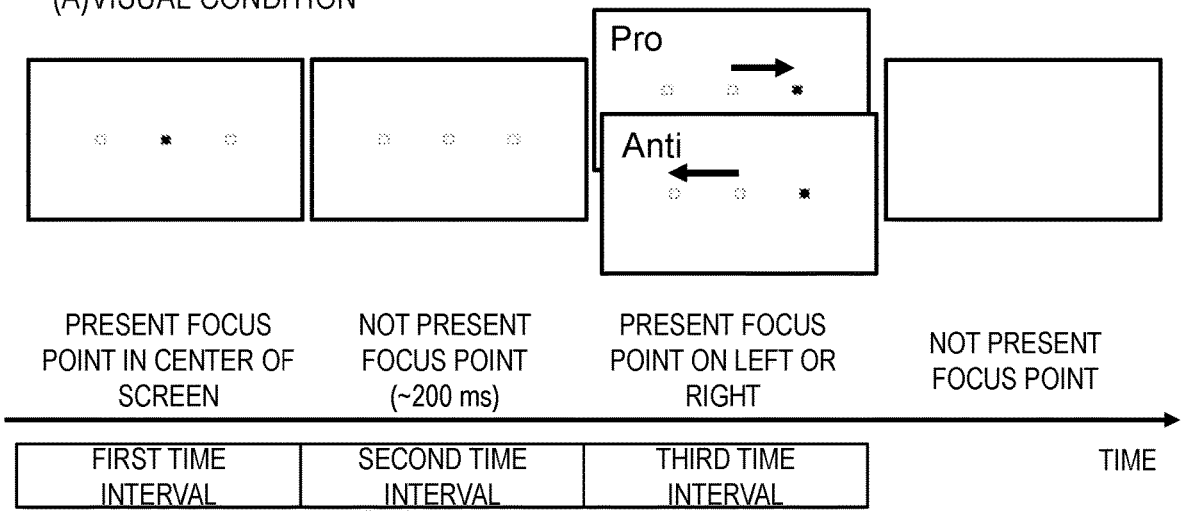
FIG. 1 is a view showing tests that serve as the basis of the present invention.
Figure 1:
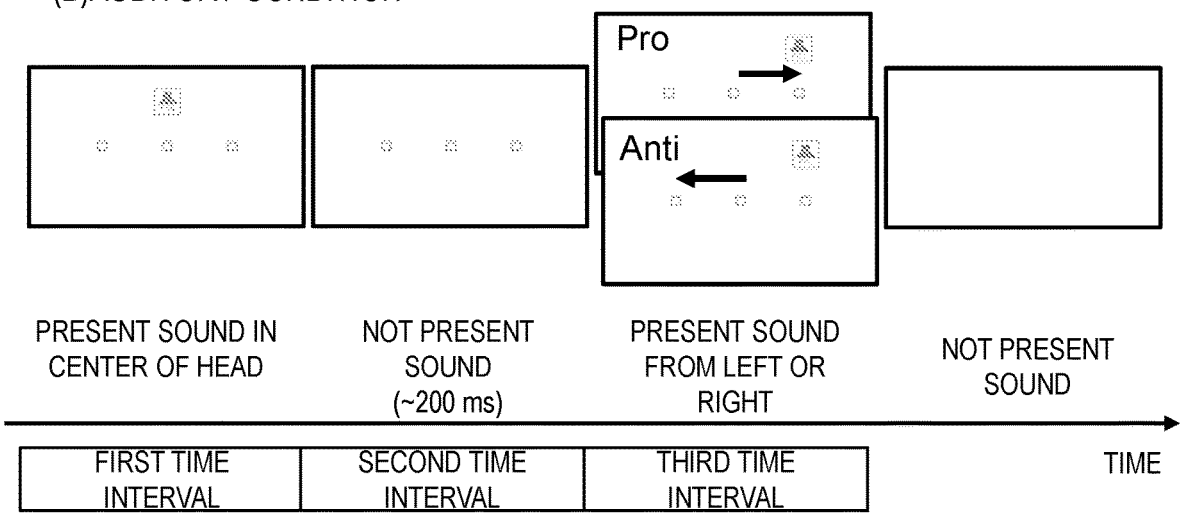

After the image of the focus point has been displayed for a fixed period of time in an initial position (the center), the image of the focus point is deleted for a fixed period of time, whereupon an image on which the position of the focus point has been moved either left or right is displayed (see FIG. 1A). Here, a time interval during which the image of the focus point is displayed in the initial position will be referred to as a "first time interval", a time interval during which the image of the focus point is deleted will be referred to as a "second time interval", and a time interval during which the image of the moved focus point is displayed will be referred to as a "third time interval". The third time interval is the time interval in which the subject executes a task involving moving the eyes, and the movement of the eyes of the subject during this time interval is captured by an infrared camera or the like, whereupon a feature value of a single saccade is extracted. It is assumed here that the feature value of the saccade is extracted from a movement of the pupil or a difference between movements of the pupil and the iris. More specifically, either a damping coefficient of a saccade performed by the pupil or a difference between the damping coefficient of the saccade performed by the pupil and a damping coefficient of a saccade performed by the iris is used as the feature value. The damping coefficient will be described in detail below.

(2) Task 1B

The image of the focus point is displayed on the display placed in front of the subject, and after a fixed period of time, the position of the focus point is moved left or right, the subject being instructed to move his/her eyes in the opposite direction to the movement direction of the focus point.

Subsequent procedures are similar to those of task 1A. Accordingly, the definitions of the first to third time intervals and the extracted feature values of the saccades are identical to those of task 1A.

[Test 2]

In test 1, the eyes are moved in accordance with the movement of the image of the focus point displayed on the display, whereas in test 2, a sound is used instead of an image. For this purpose, speakers are disposed in three locations, namely in front, on the left side, and on the right side of the subject.

(1) Task 2A

A sound that serves as an auditory cue is issued from the speaker placed in front of the subject, and after a fixed period of time, the sound is issued from the speaker on either the left side or the right side, the subject being instructed to move his/her eyes so as to follow the sound.

Subsequent procedures are similar to those of task 1A (see FIG. 1B). In other words, during the first time interval, the sound is issued from the speaker in front, and during the third time interval, the sound is issued from the speaker on either the left or the right. The feature value of the saccade is then extracted from the movement of the eyes of the subject during the third time interval. Note that headphones may be used instead of speakers.

(2) Task 2B

The sound is issued from the speaker placed in front of the subject, and after a fixed period of time, the sound is issued from the speaker on either the left side or the right side, the subject being instructed to move his/her eyes in the opposite direction to the speaker issuing the sound.

Subsequent procedures are similar to those of task 2A so that the feature value of the saccade is extracted from the movement of the eyes of the subject during the third time interval.

[Test Results]

Figure 2:
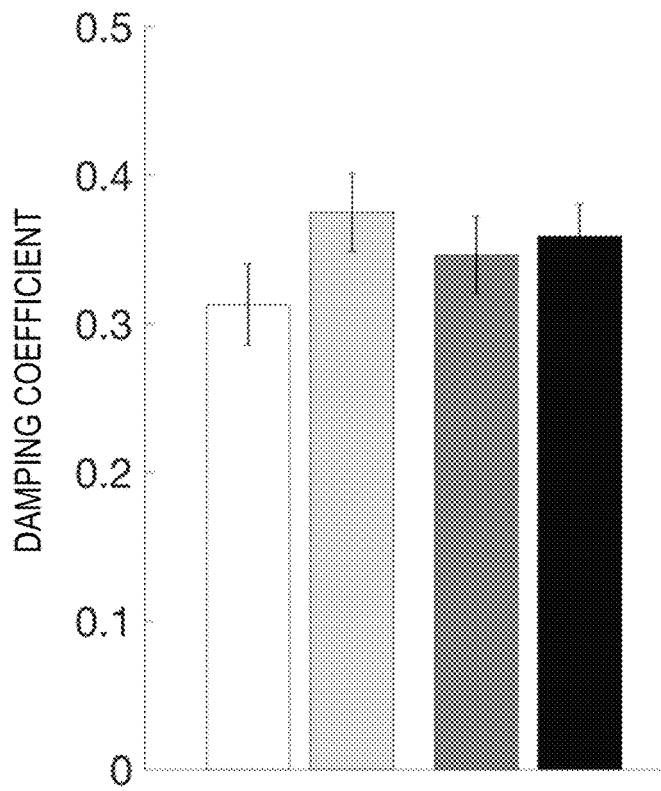
FIG. 2 is a view showing test results.
Figure 2:
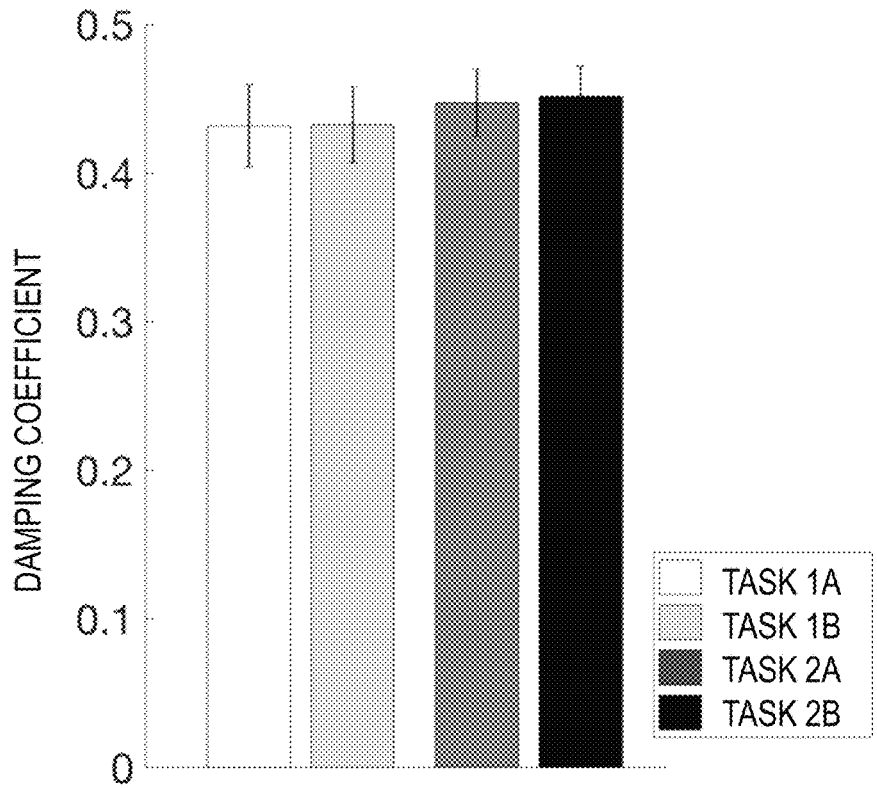

FIG. 2 is a view showing test results. The four task types, namely task 1A to task 2B, were each implemented a plurality of times on a plurality of subjects, and the value of the damping coefficient is an average value of the damping coefficients of the saccades extracted during the respective implementations. FIG. 2A shows the value of the damping coefficient extracted from the movement of the pupil in each task, and FIG. 2B shows the value of the damping coefficient extracted from the movement of the iris in each task. In both figures, the damping coefficients of task 1A, task 1B, task 2A, and task 2B are shown in order from left to right. As is evident from the test results, in the case of FIG. 2A, or in other words when focusing on the movement of the pupil (pupil movement), the damping coefficient tends to be larger in task 1B and task 2B than in task 1A and task 2A. In the case of FIG. 2B, meanwhile, or in other words when focusing on the movement of the iris (iris movement), there are no significant differences among the tasks.

Figure 3:
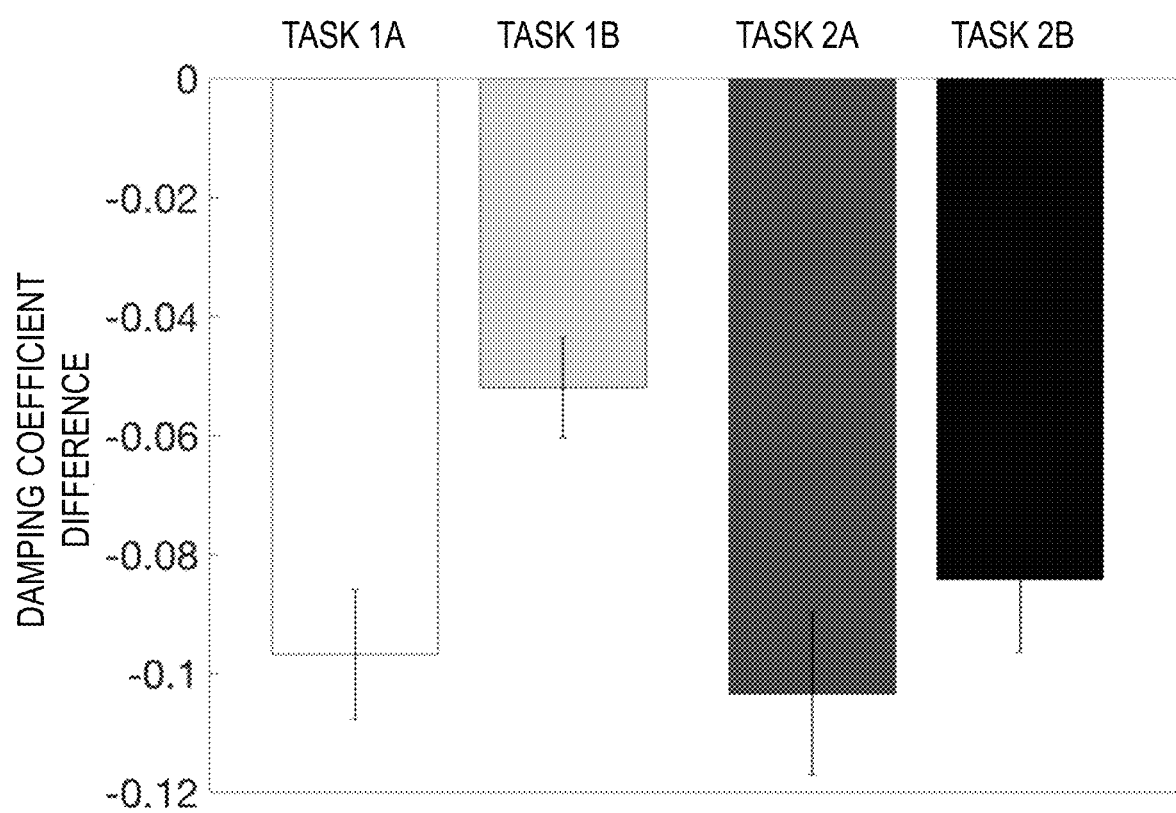
FIG. 3 is a view showing test results.

Further, in FIG. 3, the difference between the damping coefficient of the pupil movement and the damping coefficient of the iris movement is shown on the vertical axis, and a similar tendency, namely that the difference between the damping coefficients is larger in task 1B and task 2B, is evident here. Vibration (overshoot) of the iris following the saccade, although smaller than that of the pupil, is not entirely absent. Therefore, by acquiring the difference between the damping coefficient of the pupil movement and the damping coefficient of the iris movement, it becomes possible to see the pupil overshoot relative to the overshoot of the entire eyeball (movement extracted from the edge of the iris). In other words, the vibration of the pupil minus the movement of the entire eyeball can be extracted as a feature value.

Typically, when a focus point moves or a noticeable sound is issued from a specific direction, the eyes tend to move reflexively in that direction. In task 1A and task 2A, the direction in which the focus point moves/the sound is issued matches the direction in which the eyes are supposed to move, and therefore the eyes can be moved by a reflexive movement, whereas in task 1B and task 2B, the eyes must be moved consciously in the opposite direction to the reflexive movement. In other words, task 1B and task 2B may be said to correspond to a state in which eye movement is consciously controlled, while task 1A and task 2A may be said to correspond to a state in which the eyes are moved unconsciously. It may therefore be said that these test results show that the damping coefficient of a saccade performed when the eyes are moved unconsciously, i.e. reflexively, tends to be smaller than the damping coefficient of a saccade performed when eye movement is consciously controlled.

Hereafter, an eyeball movement caused by an external factor will be referred to as a pro-saccade, and a voluntary eyeball movement executed so as to suppress a pro-saccade will be referred to as an anti-saccade.

First Embodiment

A reflexivity judgement apparatus 100 judges whether or not an eyeball movement performed by a subject occurred reflexively.

Figure 4:
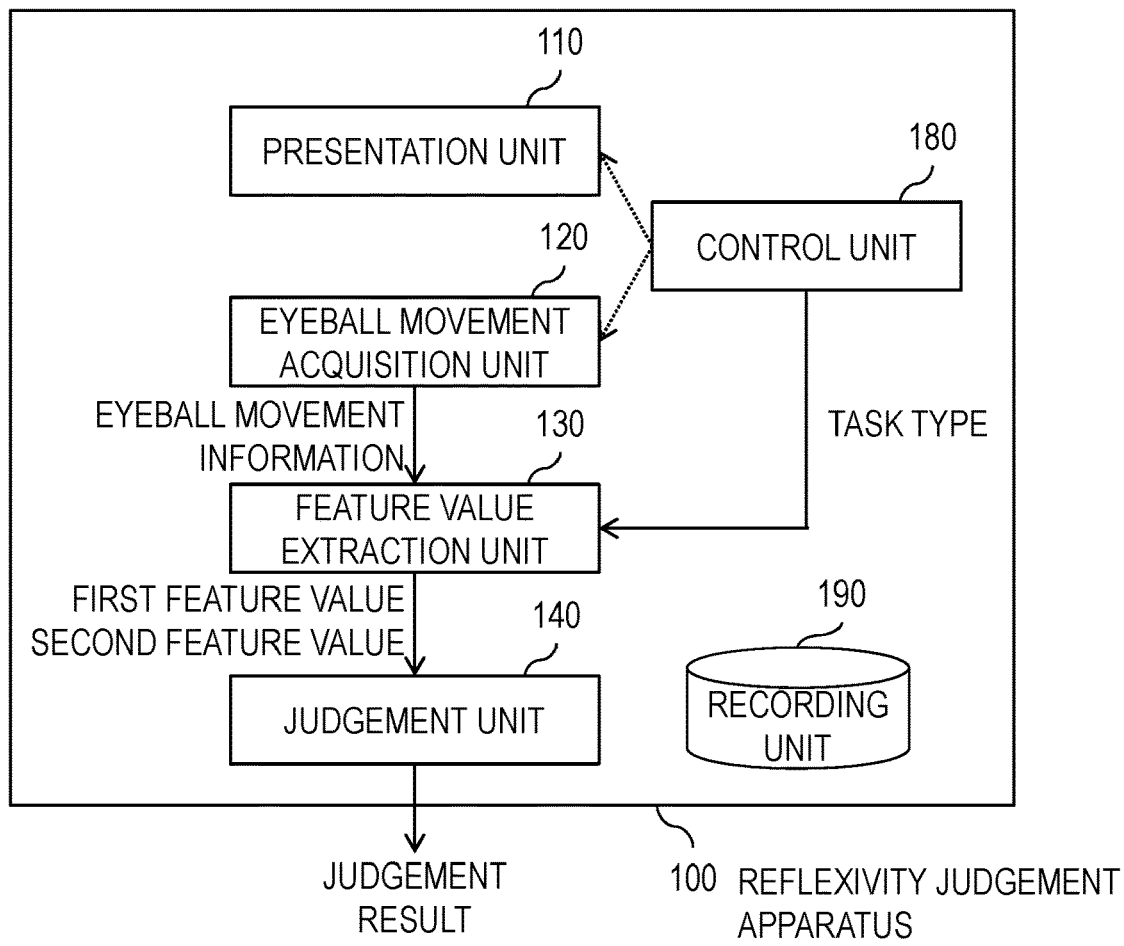
FIG. 4 is a block diagram showing an example configuration of a reflexivity judgement apparatus 100.
Figure 5:
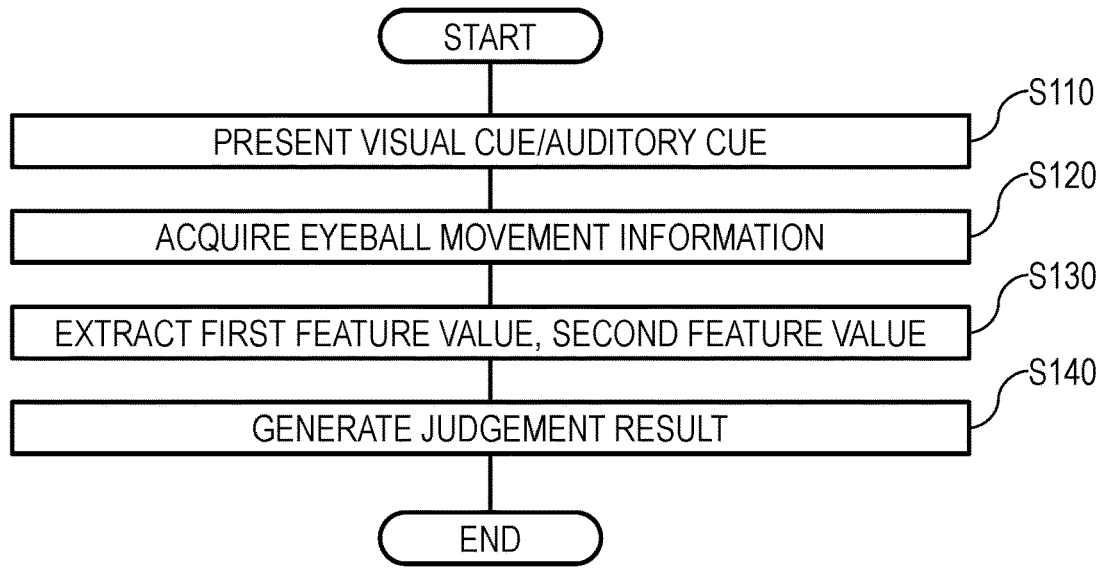
FIG. 5 is a flowchart showing an example operation of the reflexivity judgement apparatus 100.

The reflexivity judgement apparatus 100 will be described below with reference to FIGS. 4 and 5. FIG. 4 is a block diagram showing a configuration of the reflexivity judgement apparatus 100. FIG. 5 is a flowchart showing an operation of the reflexivity judgement apparatus 100. As shown in FIG. 4, the reflexivity judgement apparatus 100 includes a presentation unit 110, an eyeball movement acquisition unit 120, a feature value extraction unit 130, a judgement unit 140, a control unit 180, and a recording unit 190. The recording unit 190 is a constituent part that records information required during processing executed by the reflexivity judgement apparatus 100 as appropriate.

An operation of the reflexivity judgement apparatus 100 will be described in accordance with FIG. 5.

[Presentation Unit 110]

In S110, the presentation unit 110 presents the subject with the focus point image of task 1A or task 1B as a visual cue. More specifically, the presentation unit 110 displays the focus point image in the center of the display placed in front of the subject, then deletes the focus point image for a fixed period of time, and then displays a focus point image that has been moved from the center to either the left or the right. It is assumed that the focus point image is presented in response to an instruction from the control unit 180. Note that the position in which the focus point image is displayed at the start point of task 1A or task 1B (referred to hereafter as the initial position of the focus point) is not limited to the center of the display and may be within a predetermined error range from the center.

Note that the presentation unit 110 may present the sound of task 2A or task 2B instead of presenting the focus point image of task 1A or task 1B. In other words, in S110, the presentation unit 110 presents the subject with the sound of task 2A or task 2B as an auditory cue. More specifically, the presentation unit 110 issues the sound from the speaker placed in front of the subject, and after a period of silence lasting a fixed period of time, issues the sound from the speaker positioned on either the left side or the right side of the subject. It is assumed that the sound is presented in response to an instruction from the control unit 180.

[Control Unit 180]

The control unit 180 controls presentation of the image (sound) by the presentation unit 110, and also implements control for executing task 1A or task 1B (task 2A or task 2B) by implementing control so that the eyeball movement acquisition unit 120 acquires information relating to an eyeball movement performed by the subject while the image (sound) is being presented in the third time interval. At this time, the control unit 180 implements control so that task 1A and task 1B (task 2A and task 2B) are each executed at least once. Further, the control unit 180 outputs information specifying the task to be executed (referred to hereafter as the task type) to the feature value extraction unit 130 every time task 1A or task 1B (task 2A or task 2B) is executed.

[Eyeball Movement Acquisition Unit 120]

In S120, the eyeball movement acquisition unit 120, in response to an instruction from the control unit 180, acquires and outputs information relating to the eyeball movement performed by the subject during the third time interval. For example, a movement of the eyeball of the subject during execution of a task is captured by an infrared camera. Then, by performing image processing on the captured result, a time series of information indicating the position of the eyeball at time intervals (1000 Hz, for example) is acquired as eyeball movement information. Note that the position information may be acquired either in relation to both the left and right eyeballs or in relation to only one of the eyeballs. In this embodiment, it is assumed that the position information is acquired in relation to only one eyeball. Furthermore, here, the eyeball movement is a pupil movement, and a time series of information indicating the position of the pupil is acquired as the eyeball movement information.

[Feature Value Extraction Unit 130]

In S130, the feature value extraction unit 130 extracts and outputs a feature value (referred to hereafter as a first feature value) of the saccade appearing in the eyeball movement of the subject during task 1A or task 2A (i.e., a task involving moving the eye so as to follow the visual or auditory cue) and a feature value (referred to hereafter as a second feature value) of the saccade appearing in the eyeball movement of the subject during task 1B or task 2B (i.e., a task involving moving the eye in the opposite direction to the visual or auditory cue) from the eyeball movement information acquired in S120 and the task type, which is input from the control unit 180. Here, the first feature value and the second feature value are feature values relating to the pupil (feature values of pupil movements).

A method for extracting the first and second feature values will be described below. First, the interval in which the saccade occurs is detected from the eyeball movement information (the time series of information indicating the position of the eyeball). For example, a first-order series of differences is calculated in relation to the time series of information indicating the position of the eyeball, and the time interval in which an absolute value of the series of differences exceeds a predetermined threshold is detected as the interval in which the saccade occurs. In a case where the acquired eyeball position information is determined to include a large amount of noise or the like, a moving average value within an appropriate range may be used to calculate the first-order series of differences. A value approximately six times the standard deviation of the series of differences is preferably employed as the threshold used for detection.

Next, a feature value is extracted by modeling the time series of information indicating the position of the eyeball when the saccade occurs as a step response of a position control system. This will now be described. A step response of a position control system is expressed by the following formula, in which the natural angular frequency is set as $\omega_n$.

$$G(s) = \frac{A\omega_n^2}{s^2 + 2\zeta\omega_n s + \omega_n^2} \quad \text{[Formula 1]}$$

$$y(t) = A\left\{1 - e^{-\zeta\omega_n t}\left(\frac{\zeta}{\sqrt{1-\zeta^2}}\sin\omega_d t + \cos\omega_d t\right)\right\}$$

$$y'(t) = \frac{A\omega_n}{\sqrt{1-\zeta^2}} e^{-\zeta\omega_n t}\sin\omega_d t$$

$$\omega_d = \omega_n\sqrt{1-\zeta^2}$$

Here, G(s) represents a transfer coefficient, y(t) represents the position, and y'(t) represents a velocity. Further, a damping ratio $\lambda$, a damping coefficient $\zeta$, and the natural angular frequency $\omega_n$ are expressed respectively by the following formulae.

$$\lambda = \frac{|V_0|}{|V_{max}|} = \frac{|A_0|}{|A|} \quad \text{[Formula 2]}$$

$$\zeta = \frac{1}{\sqrt{1 + \left(\frac{\pi}{\log\lambda}\right)^2}}$$

$$\omega_n = \frac{\pi}{T_p\sqrt{1-\zeta^2}}$$

Figure 6:
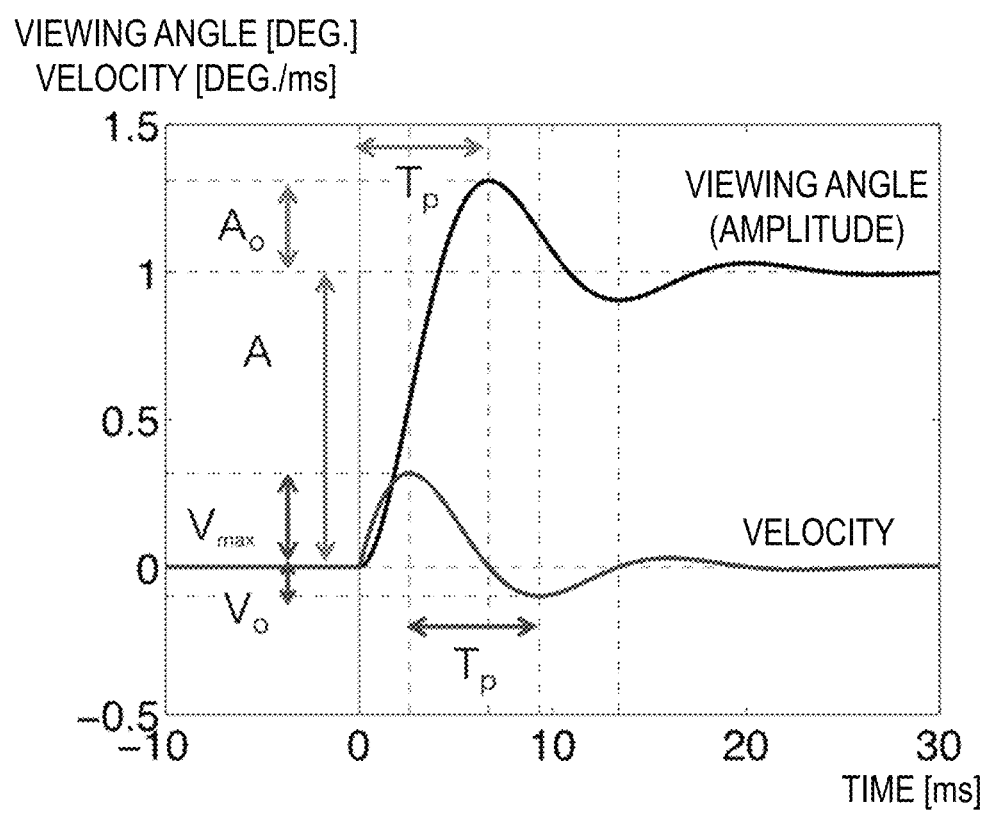
FIG. 6 is a view illustrating parameters of a step-response model.

Here, t is an index expressing a time, and s is a parameter (a complex number) generated by a Laplace transform. The natural angular frequency $\omega_n$ corresponds to an index expressing the response speed of the saccade, and the damping coefficient $\zeta$ corresponds to an index corresponding to the accuracy of the saccade response. Further, A, $V_{max}$, $A_0$, $V_0$, and $T_p$ are respectively defined as follows (see FIG. 6).

(1) Reference amplitude A: The movement amount at the point where the eyeball movement produced by the saccade converges.
(2) Maximum velocity $V_{max}$: The maximum velocity up to the point at which reference amplitude A+overshoot amplitude $A_0$ is reached.
(3) Overshoot amplitude $A_0$: The size of the part exceeding (going beyond) the reference amplitude A due to the saccade. Overshoot is a phenomenon in which a waveform projects beyond the reference amplitude A in the rising part of the waveform, or refers to the projecting waveform itself. In other words, the overshoot amplitude is the size of the projecting part.
(4) Overshoot velocity $V_0$: The maximum velocity when attempting to converge on the reference amplitude A from reference amplitude A+overshoot amplitude $A_0$.
(5) Rise time $T_p$: The time required to reach (rise to) reference amplitude A+overshoot amplitude $A_0$. Note that the time required to reach reference amplitude A+overshoot amplitude $A_0$ takes an identical value to the time required to reach the overshoot velocity $V_0$ from the maximum velocity $V_{max}$.

By modeling the time series of eyeball position information as a step response in this manner, the damping coefficient $\zeta$, the damping ratio $\lambda$, the reference amplitude A, the maximum velocity $V_{max}$, the natural angular frequency $\omega_n$, and so on are acquired as feature values of the saccade appearing during the eyeball movement.

Here, the eyeball movement information (the time series of eyeball position information) acquired by the eyeball movement acquisition unit 120 is a time series of information indicating the position of the pupil, and therefore the damping coefficient c, the damping ratio $\lambda$, the reference amplitude A, the maximum velocity $V_{max}$, and the natural angular frequency $\omega_n$ of the saccade appearing in the pupil movement can be acquired as feature values of the saccade appearing in the eyeball movement. Here, however, the damping coefficient $\zeta$ is extracted. In other words, the feature value extraction unit 130 extracts the damping coefficient of the saccade appearing in the pupil movement as the feature value of the saccade appearing in the eyeball movement.

Note that when task 1A and task 1B (task 2A and task 2B) are executed a plurality of times, respective representative values of the extracted values may be set as the first feature value and the second feature value. An average value, a median value, a maximum value, a minimum value, or the like may be used as the representative value.

[Judgement Unit 140]

In S140, the judgement unit 140 generates and outputs a judgement result indicating whether or not the eyeball movement of the subject occurred reflexively on the basis of the degree of difference between the first feature value extracted in S130 and the second feature value likewise extracted in S130. More specifically, the judgement unit 140 generates a judgement result indicating that the pupil movement of the subject occurred reflexively when the degree of difference is large, and generates a judgement result indicating that the pupil movement of the subject cannot be said to have occurred reflexively in other cases. This will now be described in detail. When $\zeta_1$ is set as the first feature value, $\zeta_2$ is set as the second feature value, and $\Delta$ ($\Delta \geq 0$) is set as a predetermined value, and a difference $\zeta_2 - \zeta_1$ between the second feature value and the first feature value is either larger than the predetermined value $\Delta$ or no smaller than the predetermined value $\Delta$, a judgement result indicating that the pupil movement of the subject occurred reflexively is generated, and in other cases, a judgement result indicating that the pupil movement of the subject cannot be said to have occurred reflexively is generated. Note that by setting $\Delta$ at $\Delta > 0$, an error can be permitted when determining the magnitude relationship.

Note that in this embodiment, whether or not the eyeball movement occurred reflexively is judged on the basis of the feature value of the pupil movement. Here, as described in the <Technical Background>, the reason why the "pupil" is set as the subject of feature value extraction is that the pupil of the eye is where significant differences appear in the feature value. Nevertheless, a reflexive eye movement is a movement of the entire eyeball, and therefore "eyeball movement" is set as the subject of the judgement.

(First Modification)

In the above description, the damping coefficient of the saccade appearing in the pupil movement is used as the feature value, but an element that has either a positive correlative relationship or a negative correlative relationship with the damping coefficient of the saccade appearing in the pupil movement may be used instead of the damping coefficient. For example, the damping ratio of the saccade appearing in the pupil movement may be used. The damping ratio has a negative correlative relationship with the damping coefficient. In this case, the eyeball movement information (the time series of information indicating the position of the eyeball) acquired by the eyeball movement acquisition unit 120 is set as a time series of information indicating the position of the pupil, and the feature value extraction unit 130 extracts the damping ratio of the saccade appearing in the pupil movement as the feature value of the saccade appearing in the eyeball movement. Further, the judgement unit 140 sets a damping ratio $\lambda_1$, a damping ratio $\lambda_2$, and $\Delta$ ($\Delta \geq 0$) as the first feature value, the second feature value, and the predetermined value, respectively, generates a judgement result indicating that the eyeball movement of the subject occurred reflexively when a difference $\lambda_1 - \lambda_2$ between the first feature value and the second feature value is either larger than the predetermined value $\Delta$ or no smaller than the predetermined value $\Delta$, and generates a judgement result indicating that the eyeball movement of the subject cannot be said to have occurred reflexively in other cases.

With the embodiment according to the present invention, it is possible to judge the reflexivity of an eyeball movement. More specifically, it is possible to judge whether or not an eyeball movement by a subject occurred reflexively.

Second Embodiment

A reflexivity judgement apparatus 200 judges whether or not the eye of the subject is likely to move reflexively.

Figure 7:
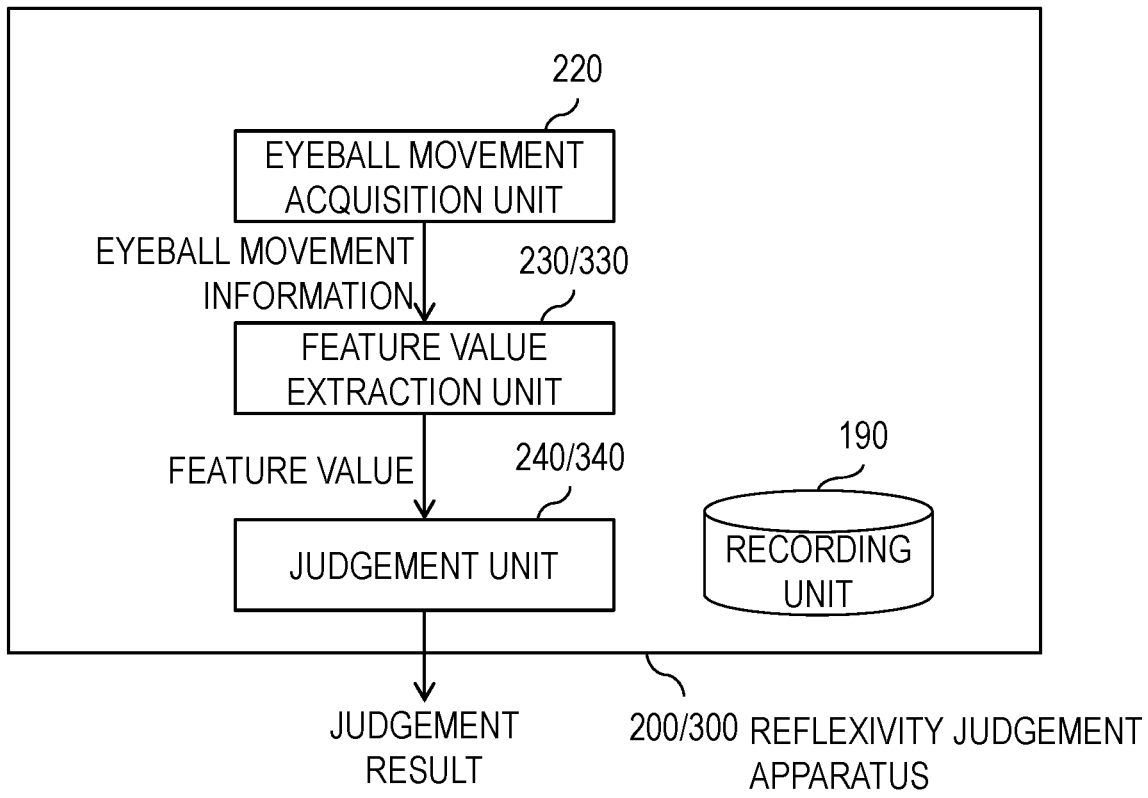
FIG. 7 is a block diagram showing an example configuration of a reflexivity judgement apparatus 200/300.
Figure 8:
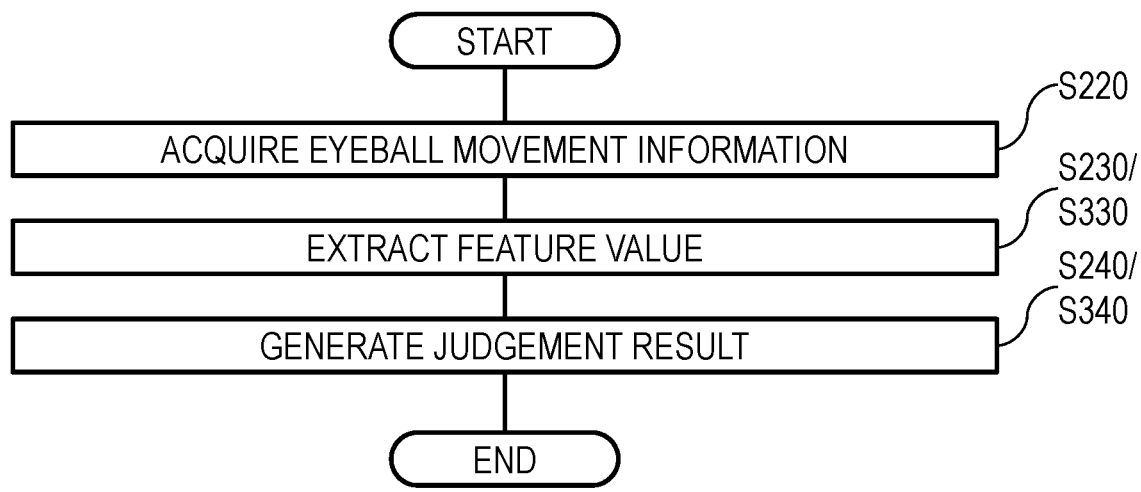
FIG. 8 is a flowchart showing an example operation of the reflexivity judgement apparatus 200/300.

The reflexivity judgement apparatus 200 will be described below with reference to FIGS. 7 and 8. FIG. 7 is a block diagram showing the configuration of the reflexivity judgement apparatus 200. FIG. 8 is a flowchart showing an operation of the reflexivity judgement apparatus 200. As shown in FIG. 7, the reflexivity judgement apparatus 200 includes an eyeball movement acquisition unit 220, a feature value extraction unit 230, a judgement unit 240, and the recording unit 190. The recording unit 190 is a constituent part that records information required during processing executed by the reflexivity judgement apparatus 200 as appropriate. For example, a reference value constituted by a feature value of a saccade appearing in an eyeball movement performed by the subject in a state of concentration is recorded in the recording unit 190 in advance. The reference value is prepared by the following procedure, for example. By having the subject execute task 1B (task 2B), information relating to an eyeball movement performed by the subject in the third time interval is acquired, and from this information, the feature value of the saccade appearing in the eyeball movement is extracted. This procedure is repeated a plurality of times, and a representative value thereof is set as the reference value. An average value, a median value, a maximum value, a minimum value, or the like may be used as the representative value. Note that the same feature value as the feature value of the saccade appearing in the eyeball movement that is extracted by the feature value extraction unit 230 must be used as the feature value of the saccade appearing in the eyeball movement that is set as the reference value.

An operation of the reflexivity judgement apparatus 200 will be described in accordance with FIG. 8.

[Eyeball Movement Acquisition Unit 220]

In S220, the eyeball movement acquisition unit 220 acquires and outputs information relating to an eyeball movement performed by the subject in a predetermined time interval. A similar method to that of the eyeball movement acquisition unit 120 may be used to acquire the eyeball movement information. Furthermore, here, a time series of information indicating the position of the pupil is acquired as the eyeball movement information.

[Feature Value Extraction Unit 230]

In S230, the feature value extraction unit 230 extracts and outputs the feature value of the saccade appearing in the eyeball movement of the subject from the eyeball movement information acquired in S220. A similar method to that of the feature value extraction unit 130 may be used to extract the feature value. Furthermore, the damping coefficient of the saccade appearing in the pupil movement is extracted as the feature value of the saccade appearing in the eyeball movement.

Note that when the extraction procedure is executed a plurality of times, a representative value of the extracted values may be set as the feature value. An average value, a median value, a maximum value, a minimum value, or the like may be used as the representative value. A representative value may likewise be set as the feature value when a plurality of intervals in which saccades occur are detected within the predetermined time interval.

[Judgement Unit 240]

In S240, the judgement unit 240 generates and outputs a judgement result indicating whether or not the eye of the subject is likely to move reflexively on the basis of the degree of difference between the reference value recorded in the recording unit 190 and the feature value extracted in S230. More specifically, the judgement unit 240 generates a judgement result indicating that the eye of the subject is likely to move reflexively when the degree of difference is large, and generates a judgement result indicating that the eye of the subject cannot be considered likely to move reflexively in other cases. This will now be described in detail. When $\zeta$ is set as the feature value, $\zeta_c$ is set as the reference value, and $\Delta$ ($\Delta \geq 0$) is set as a predetermined value, and a difference $\zeta_c - \zeta$ between the reference value and the feature value is either larger than the predetermined value $\Delta$ or no smaller than the predetermined value $\Delta$, a judgement result indicating that the eye of the subject is likely to move reflexively is generated, and in other cases, a judgement result indicating that the eye of the subject cannot be considered likely to move reflexively is generated. In other words, when the feature value $\zeta$ is smaller than the reference value $\zeta_c$, the eye of the subject is judged to be likely to move reflexively. Note that by setting $\Delta$ at $\Delta > 0$, an error can be permitted when determining the magnitude relationship.

(First Modification)

In the above description, the damping coefficient of the saccade appearing in the pupil movement was used as the feature value/reference value, but an element that has either a positive correlative relationship or a negative correlative relationship with the damping coefficient of the saccade appearing in the pupil movement may be used instead of the damping coefficient. For example, the damping ratio of the saccade appearing in the pupil movement may be used. The damping ratio has a negative correlative relationship with the damping coefficient. In this case, the eyeball movement information (the time series of information indicating the position of the eyeball) acquired by the eyeball movement acquisition unit 220 is set as a time series of information indicating the position of the pupil, and the feature value extraction unit 230 extracts the damping ratio of the saccade appearing in the pupil movement as the feature value of the saccade appearing in the eyeball movement. Further, the judgement unit 240 sets $\lambda$ as the feature value, $\lambda_c$ as the reference value, and $\Delta$ ($\Delta \geq 0$) as the predetermined value, generates a judgement result indicating that the eye of the subject is likely to move reflexively when a difference $\lambda - \lambda_c$ between the feature value and the reference value is either larger than the predetermined value $\Delta$ or no smaller than the predetermined value $\Delta$, and generates a judgement result indicating that the eye of the subject cannot be considered likely to move reflexively in other cases.

(Second Modification)

A time series of information indicating the position of the pupil and a time series of information indicating the position of the iris may be set as the eyeball movement information (the time series of information indicating the position of the eyeball) acquired by the eyeball movement acquisition unit 220, and a difference between the damping coefficient of the saccade appearing in the pupil movement and the damping coefficient of the saccade appearing in the iris movement may be set as the feature value of the saccade appearing in the eyeball movement, extracted by the feature value extraction unit 230. In this case, the eyeball movement acquisition unit 220 acquires a time series of information indicating the position of the pupil and a time series of information indicating the position of the iris as the eyeball movement information. Further, the feature value extraction unit 230 determines the damping coefficient of the saccade appearing in the pupil movement and the damping coefficient of the saccade appearing in the iris movement respectively from the time series of information indicating the position of the pupil and the time series of information indicating the position of the iris, acquired in S220 as the eyeball movement information, and then extracts and outputs the difference between the damping coefficient of the saccade appearing in the pupil movement and the damping coefficient of the saccade appearing in the iris movement (in other words, "damping coefficient of saccade appearing in pupil movement"-"damping coefficient of saccade appearing in iris movement") as the feature value of the saccade appearing in the eyeball movement of the subject. Note that the feature value of the saccade appearing in the iris movement, similarly to the feature value of the saccade appearing in the pupil movement, may be determined using a step response model. Furthermore, the judgement unit 240 sets α as the feature value (in other words, "damping coefficient of saccade appearing in pupil movement"−"damping coefficient of saccade appearing in iris movement"), $\alpha_c$ as the reference value, and Δ (Δ≥0) as the predetermined value, generates a judgement result indicating that the eye of the subject is likely to move reflexively when a difference $\alpha_c-\alpha$ between the reference value and the feature value is either larger than the predetermined value Δ or no smaller than the predetermined value Δ, and generates a judgement result indicating that the eye of the subject cannot be considered likely to move reflexively in other cases.

In another example, the damping ratio of the saccade appearing in the pupil movement and the damping ratio of the saccade appearing in the iris movement may be used instead of the damping coefficient of the saccade appearing in the pupil movement and the damping coefficient of the saccade appearing in the iris movement. In this case, the eyeball movement acquisition unit 220 acquires a time series of information indicating the position of the pupil and a time series of information indicating the position of the iris as the eyeball movement information. Further, the feature value extraction unit 230 determines the damping ratio of the saccade appearing in the pupil movement and the damping ratio of the saccade appearing in the iris movement respectively from the time series of information indicating the position of the pupil and the time series of information indicating the position of the iris, acquired in S220 as the eyeball movement information, and then extracts and outputs the difference between the damping ratio of the saccade appearing in the pupil movement and the damping ratio of the saccade appearing in the iris movement (in other words, "damping ratio of saccade appearing in pupil movement"−"damping ratio of saccade appearing in iris movement") as the feature value of the saccade appearing in the eyeball movement of the subject. Furthermore, the judgement unit 240 sets β as the feature value (in other words, "damping ratio of saccade appearing in pupil movement"−"damping ratio of saccade appearing in iris movement"), $\beta_c$ as the reference value, and Δ (Δ≥0) as the predetermined value, generates a judgement result indicating that the eye of the subject is likely to move reflexively when a difference $\beta-\beta_c$ between the feature value and the reference value is either larger than the predetermined value Δ or no smaller than the predetermined value Δ, and generates a judgement result indicating that the eye of the subject cannot be considered likely to move reflexively in other cases.

With the embodiment according to the present invention, it is possible to judge the reflexivity of an eyeball movement. More specifically, it is possible to judge whether or not the eye of the subject is likely to move reflexively.

Third Embodiment

As noted above, the reference amplitude, the maximum velocity, the natural angular frequency, and so on exist as feature values as well as the damping coefficient and the damping ratio. Here, an embodiment in which the judgement as to whether or not the eye of the subject is likely to move reflexively is made using a feature value combining these feature values with the damping coefficient or the damping ratio will be described. At this time, a reflexivity judgement model into which the aforesaid feature value, which is learned by a machine learning method, is input as the feature value of the saccade appearing in the eyeball movement, and which outputs a judgement result indicating whether or not the eye is likely to move reflexively is used. As a result, a judgement result exhibiting a higher degree of precision can be generated.

A reflexivity judgement apparatus 300, similarly to the reflexivity judgement apparatus 200, judges whether or not the eye of the subject is likely to move reflexively.

The reflexivity judgement apparatus 300 will be described below with reference to FIGS. 7 and 8. FIG. 7 is a block diagram showing the configuration of the reflexivity judgement apparatus 300. FIG. 8 is a flowchart showing an operation of the reflexivity judgement apparatus 300. As shown in FIG. 7, the reflexivity judgement apparatus 300 includes the eyeball movement acquisition unit 220, a feature value extraction unit 330, a judgement unit 340, and the recording unit 190. The recording unit 190 is a constituent part that records information required during processing executed by the reflexivity judgement apparatus 300 as appropriate. For example, a reflexivity judgement model is recorded in advance in the recording unit 190. Here, the reflexivity judgement model is a learned model learned by a machine learning method to output a judgement result indicating whether or not the eye is likely to move reflexively in response to input of a feature value of a saccade appearing in an eyeball movement. The input feature value is assumed to include at least one of a feature value (the damping coefficient, for example) having a positive correlative relationship with the damping coefficient and a feature value (the damping ratio, for example) having a negative correlative relationship with the damping coefficient. More specifically, the feature value is assumed to include at least one of the damping coefficient of the saccade appearing in the pupil movement, the difference between the damping coefficient of the saccade appearing in the pupil movement and the damping coefficient of the saccade appearing in the iris movement, the damping ratio of the saccade appearing in the pupil movement, and the difference between the damping ratio of the saccade appearing in the pupil movement and the damping ratio of the saccade appearing in the iris movement. The maximum velocity, the reference amplitude, the natural angular frequency, and so on may also be included as feature values.

A method for learning the reflexivity judgement model will be described below.

An operation of the reflexivity judgement apparatus 300 will be described in accordance with FIG. 8.

[Eyeball Movement Acquisition Unit 220]

In S220, the eyeball movement acquisition unit 220 acquires and outputs information relating to an eyeball movement performed by the subject in a predetermined time interval. Note that as the eyeball movement information, the eyeball movement acquisition unit 220 acquires either only a time series of information indicating the position of the pupil or both a time series of information indicating the position of the pupil and a time series of information indicating the position of the iris. The information to be acquired is determined according to the feature value to be used as the input of the reflexivity judgement model.

[Feature Value Extraction Unit 330]

In S330, the feature value extraction unit 330 extracts and outputs the feature value of the saccade appearing in the eyeball movement of the subject from the eyeball movement information acquired in S220. The feature value may be determined using a step response model, in a similar manner to the feature value extraction unit 130. The feature value extracted here is identical to the feature value serving as the input of the reflexivity judgement model. For example, when the input of the reflexivity judgement model is a group including the damping coefficient, the maximum velocity, and the reference amplitude of the saccade appearing in the pupil movement, the feature value extraction unit 330 extracts the damping coefficient, the maximum velocity, and the reference amplitude of the saccade appearing in the pupil movement.

[Judgement Unit 340]

In S340, the judgement unit 340 uses the reflexivity judgement model recorded in the recording unit 190 to generate and output a judgement result indicating whether or not the eye of the subject is likely to move reflexively from the feature value of the saccade appearing in the eyeball movement of the subject, extracted in S330.

With the embodiment according to the present invention, it is possible to judge the reflexivity of an eyeball movement. More specifically, it is possible to judge whether or not the eye of the subject is likely to move reflexively.

Fourth Embodiment

A reflexivity judgement model learning apparatus 400 learns the reflexivity judgement model used by the reflexivity judgement apparatus 300.

Figure 9:
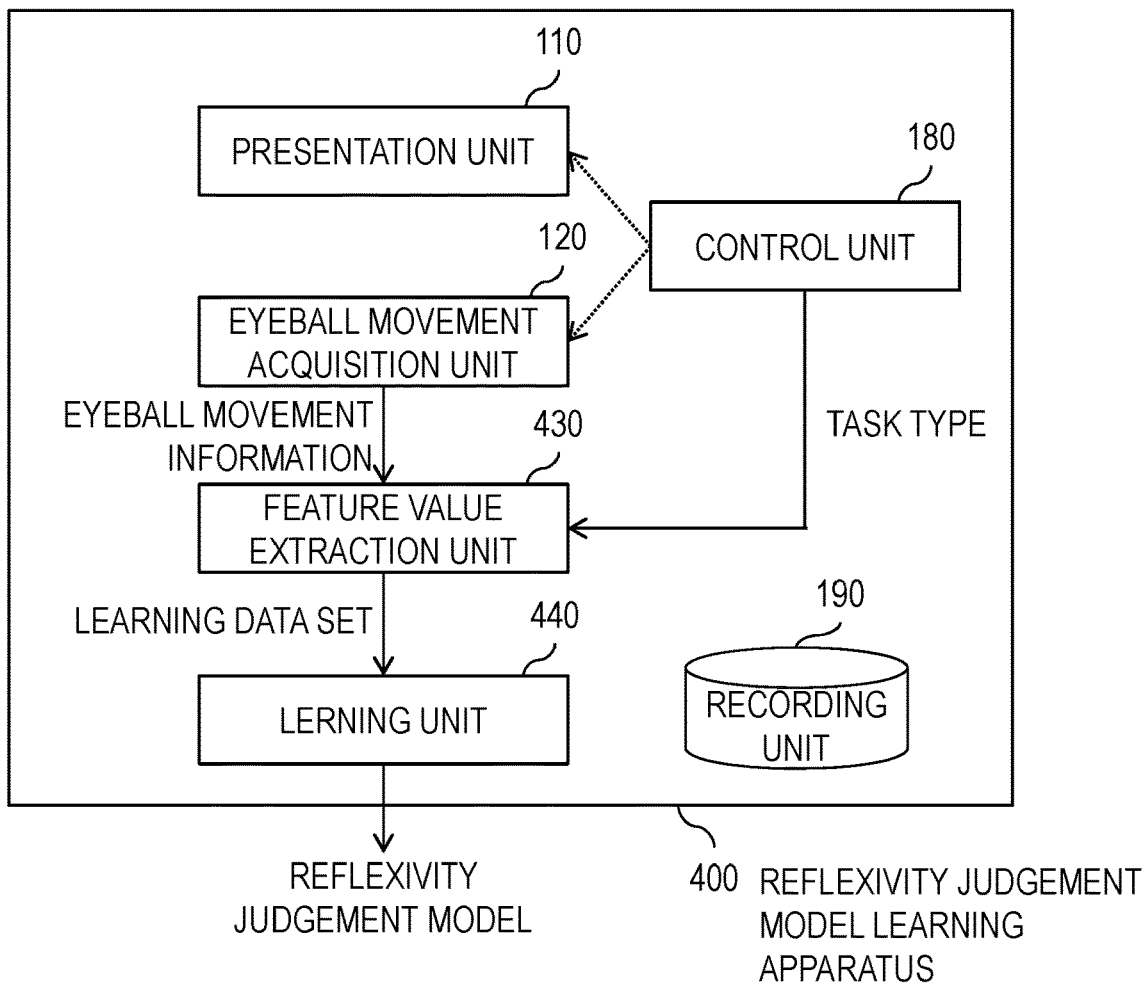
FIG. 9 is a block diagram showing an example configuration of a reflexivity judgement model learning apparatus 400.
Figure 10:
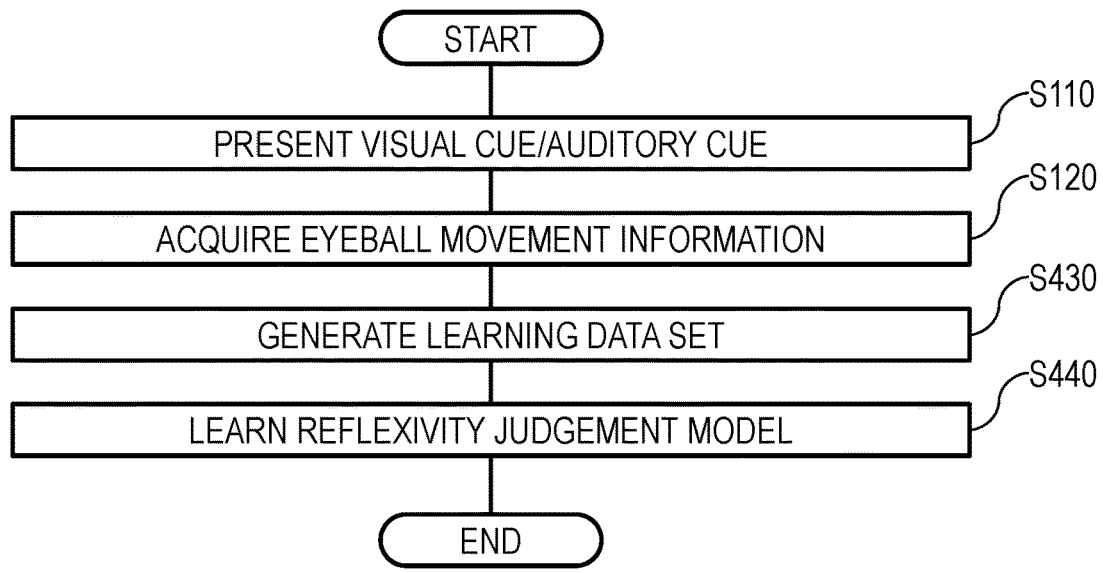
FIG. 10 is a flowchart showing an example operation of the reflexivity judgement model learning apparatus 400.

The reflexivity judgement model learning apparatus 400 will be described below with reference to FIGS. 9 and 10. FIG. 9 is a block diagram showing the configuration of the reflexivity judgement model learning apparatus 400. FIG. 10 is a flowchart showing an operation of the reflexivity judgement model learning apparatus 400. As shown in FIG. 9, the reflexivity judgement model learning apparatus 400 includes the presentation unit 110, the eyeball movement acquisition unit 120, a feature value extraction unit 430, a learning unit 440, the control unit 180, and the recording unit 190. The recording unit 190 is a constituent part that records information required during processing executed by the reflexivity judgement model learning apparatus 400 as appropriate.

An operation of the reflexivity judgement model learning apparatus 400 will be described in accordance with FIG. 10.

[Eyeball Movement Acquisition Unit 120]

In S120, the eyeball movement acquisition unit 120, in response to an instruction from the control unit 180, acquires and outputs information relating to the eyeball movement performed by the subject during the third time interval. Note that when only the feature value of the saccade appearing in the pupil movement is used as the feature value of the saccade appearing in the eyeball movement, the eyeball movement acquisition unit 120 acquires only a time series of information indicating the position of the pupil as the eyeball movement information. Further, when the feature value of the saccade appearing in the pupil movement and the feature value of the saccade appearing in the iris movement are used as the feature value of the saccade appearing in the eyeball movement, the eyeball movement acquisition unit 120 acquires a time series of information indicating the position of the pupil and a time series of information indicating the position of the iris as the eyeball movement information.

[Feature Value Extraction Unit 430]

In S430, the feature value extraction unit 430 generates and outputs a group including the feature value of the saccade appearing in the eyeball movement of the subject and an output label as learning data by extracting the feature value from the eyeball movement information acquired in S120 using the eyeball movement information and the task type, which is input from the control unit 180, as input. The feature value extracted here is identical to the feature value serving as the input of the reflexivity judgement model. Note that the output label that serves as an element of the learning data is a label attached in accordance with the task type, and corresponds to a correct answer label. When the task type is task 1A or task 2A, a label indicating that the eye of the subject is likely to move reflexively is set as the output label, and when the task type is task 1B or task 2B, a label indicating that the eye of the subject cannot be considered likely to move reflexively (i.e., is unlikely to move reflexively) is set as the output label. The generated learning data are recorded in the recording unit 190.

Note that the feature value may be determined using a step response model, in a similar manner to the feature value extraction unit 130.

A set of the learning data generated in S430 will be referred to as a learning data set. The learning data set is generated by having the control unit 180 execute task 1A or task 2A (a task involving moving the eye so as to follow a visual or auditory cue) and task 1B or task 2B (a task involving moving the eye in the opposite direction to the visual or auditory cue) a plurality of times each.

[Learning Unit 440]

In S440, the learning unit 440 learns the reflexivity judgement model using the learning data set constituted by a set of the learning data generated in S430.

A support vector machine (SVM) or a neural network, for example, can be used to learn the reflexivity judgement model. In the case of an SVM, the feature value is handled as a vector (referred to hereafter as a feature value vector), and a hyperplane separating (identifying) a point group corresponding to a feature value vector of the saccade occurring during the task that involves moving the eye so as to follow a visual or auditory cue (a point group forming a feature value vector that corresponds to a label indicating that the eye is likely to move reflexively) from a point group corresponding to a feature value vector of the saccade occurring during the task that involves moving the eye in the opposite direction to the visual or auditory cue (a point group forming a feature value vector that corresponds to a label indicating that the eye cannot be considered likely to move reflexively (i.e., is unlikely to move reflexively)) is determined within a feature value vector space. In so doing, it is possible to learn a classifier (a learned model) which, when an unknown saccade feature value (feature value vector) is input, generates a label (a judgement result) indicating whether or not the eye is likely to move reflexively in accordance with the side of the hyperplane to which the feature value vector belongs. In other words, the classifier is learned to generate a judgement result indicating that the eye of the subject is likely to move reflexively when the feature value vector is on the side of the point group corresponding to the feature value vector of the saccade occurring during the task that involves moving the eyes so as to follow the visual or auditory cue, and to generate a judgement result indicating that the eye of the subject cannot be considered likely to move reflexively when the feature value vector is on the side of the point group corresponding to the feature value vector of the saccade occurring during the task that involves moving the eyes in the opposite direction to the visual or auditory cue.

Further, in the case of a neural network, the model is learned by updating respective parameters of the neural network so that an output result (an output label estimation result) acquired when the feature value of the saccade appearing in the eyeball movement, which is an element of the learning data, is input into the neural network is the output label (the correct answer output label) that forms a group with the same feature value in the learning data. A well-known algorithm may be used as a learning algorithm. Moreover, learning is preferably started after setting appropriate initial values as the respective parameters of the neural network.

(First Modification)

The learning data used for learning by the reflexivity judgement model learning apparatus 400 were generated on the basis of task 1A and task 1B (task 2A and task 2B), but as long as a group including a saccade feature value acquired from the subject in a situation where it is possible to distinguish between a state in which the eyes of the subject are moving reflexively and a state in which the eyes are not moving reflexively and the state at that time (the correct answer output label) can be generated as the learning data, the learning data may be generated from any task.

With the embodiment according to the present invention, it is possible to learn a reflexivity judgement model used to judge the reflexivity of an eyeball movement.

Fifth Embodiment

In the first to third embodiments, the reflexivity of the eyeball movement of the subject was judged by comparing feature values extracted from a single subject. Here, an embodiment in which the reflexivity of the eyeball movement of a certain subject is judged by comparing the feature values of a plurality of subjects will be described.

First, background test results will be described.

[Background Test Results]

Figure 11:
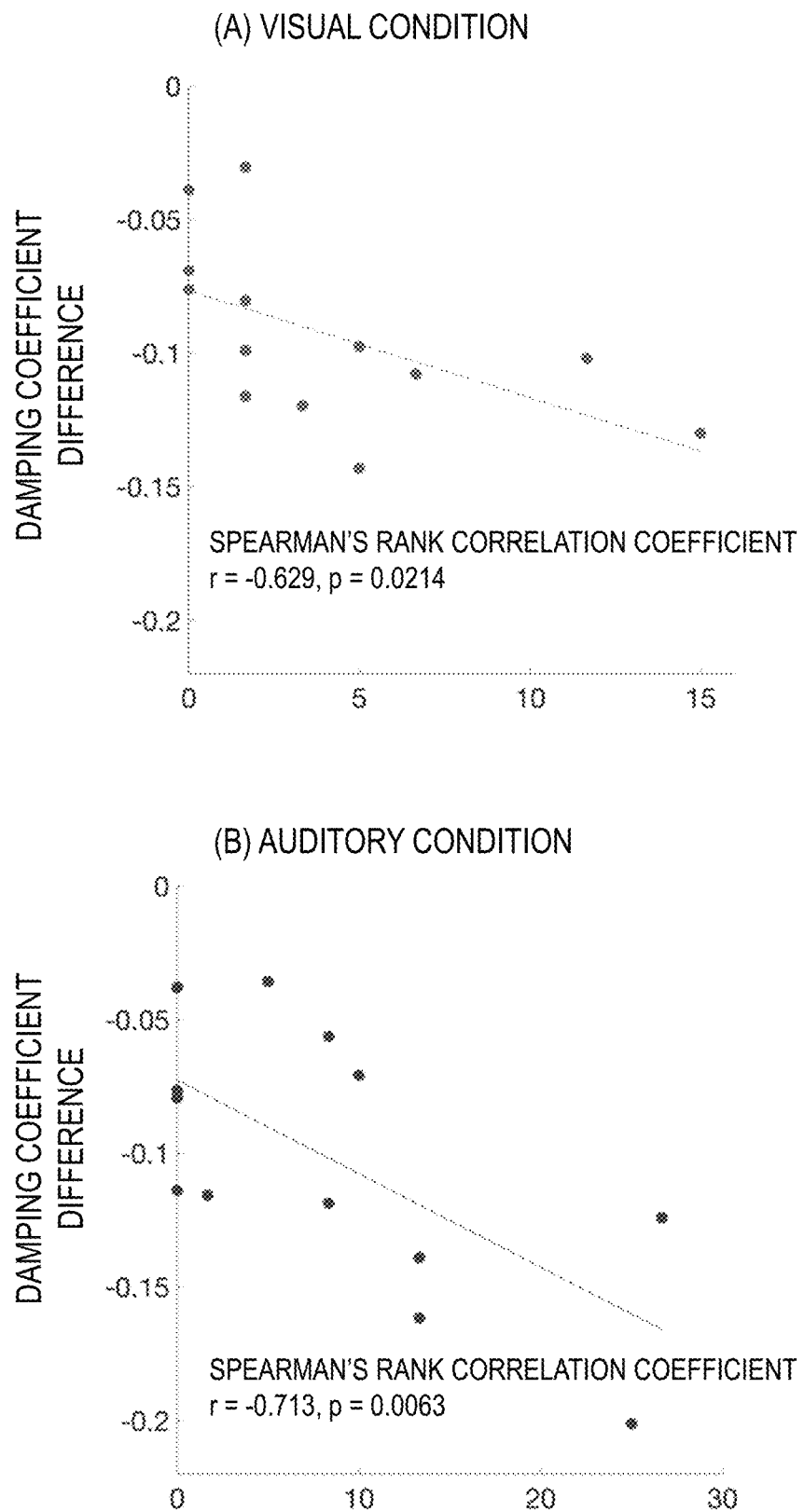
FIG. 11 is a view showing test results.

When a plurality of subjects were caused to execute task 1A and task 1B (or task 2A and task 2B), a tendency such as that shown in FIG. 11 was observed. The horizontal axis of FIG. 11 is a ratio (an error rate) of the number of times a certain subject executed task 1B/task 2B (i.e. the anti-saccade task) erroneously by orienting the eyes in a forward direction (the movement direction of the focus point) to the total number of times the subject executed the task. Further, the vertical axis of FIG. 11 is the difference between the damping coefficient of the pupil movement and the damping coefficient of the iris movement during task 1A/task 2A (i.e. the pro-saccade task) executed by the certain subject. In other words, FIG. 11 plots the error rate and the damping coefficient difference with respect to each subject. FIG. 11 shows that a subject with a high error rate tends to have a smaller damping coefficient difference than a subject with a low error rate. From this result, it may be assumed that subjects with a smaller damping coefficient difference tend to be more likely to make a mistake during the task and are more susceptible to their reflexes than subjects with a larger damping coefficient difference.

This embodiment according to the present invention is based on the discovery of the natural law described above.

A reflexivity judgement apparatus 500 judges whether or not the eye of a subject is susceptible to reflexes.

Figure 12:
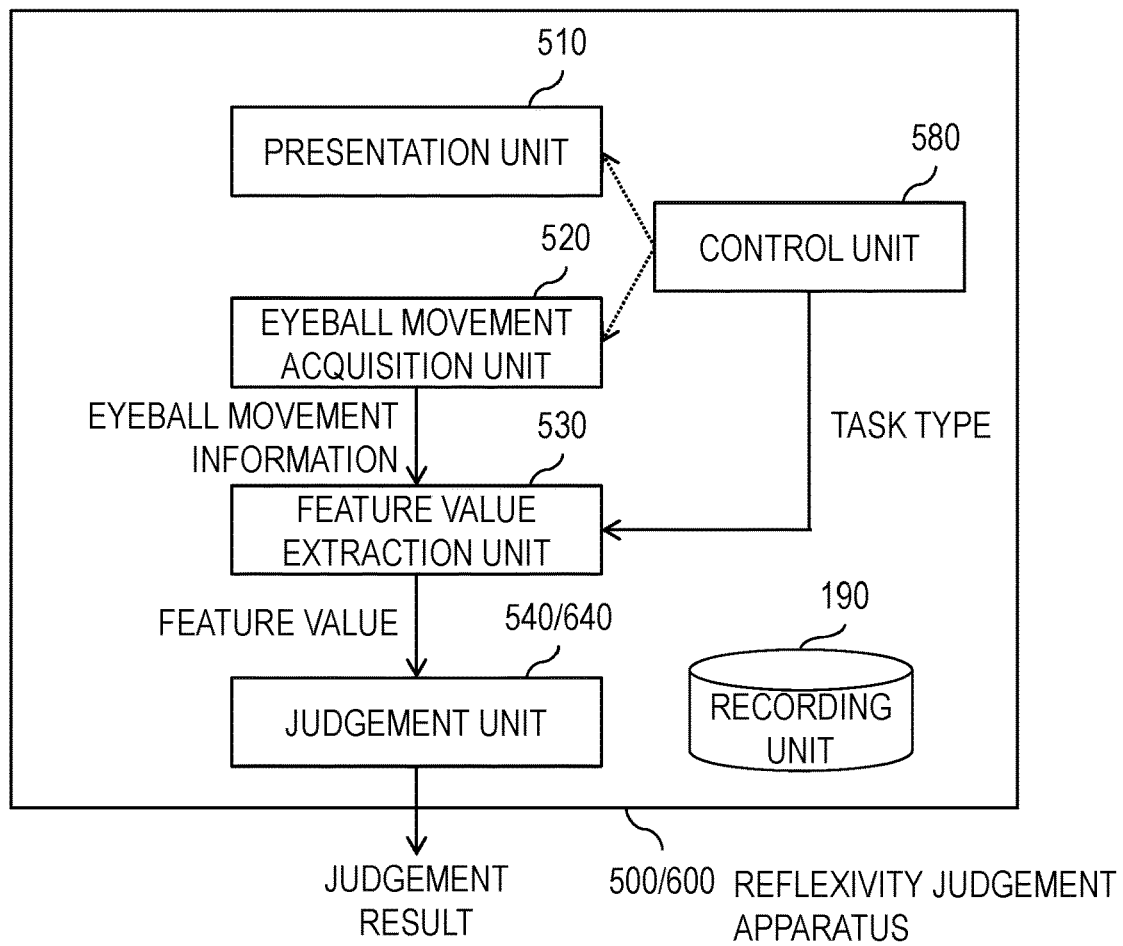
FIG. 12 is a block diagram showing an example configuration of a reflexivity judgement apparatus 500/600.
Figure 13:
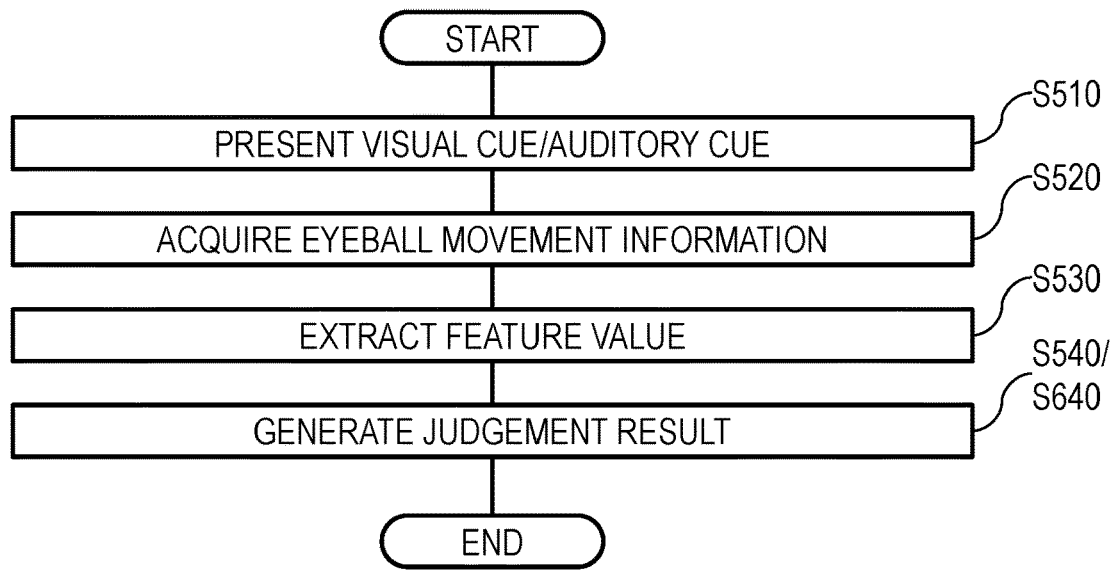
FIG. 13 is a flowchart showing an example operation of the reflexivity judgement apparatus 500/600.

The reflexivity judgement apparatus 500 will be described below with reference to FIGS. 12 and 13. FIG. 12 is a block diagram showing the configuration of the reflexivity judgement apparatus 500. FIG. 13 is a flowchart showing an operation of the reflexivity judgement apparatus 500. As shown in FIG. 12, the reflexivity judgement apparatus 500 includes a presentation unit 510, an eyeball movement acquisition unit 520, a feature value extraction unit 530, a judgement unit 540, a control unit 580, and the recording unit 190. The recording unit 190 is a constituent part that records information required during processing executed by the reflexivity judgement apparatus 500 as appropriate. For example, a reference value constituted by the feature value of the saccade appearing in the eyeball movement is recorded in the recording unit 190 in advance. Here, the difference between the damping coefficient of the saccade appearing in the pupil movement and the damping coefficient of the saccade appearing in the iris movement is used as the feature value of the saccade appearing in the eyeball movement. The reference value is prepared by the following procedure, for example. By having the subject execute task 1A (task 2A), information relating to an eyeball movement performed by the subject in the third time interval is acquired, and from this information, the difference between the damping coefficient of the saccade appearing in the pupil movement and the damping coefficient of the saccade appearing in the iris movement is extracted as the feature value of the saccade appearing in the eyeball movement of the subject. This procedure is repeated a plurality of times. Moreover, the operation is performed on a plurality of subjects. A representative value of the differences acquired in this manner is set as the reference value. An average value, a median value, a maximum value, a minimum value, or the like may be used as the representative value.

An operation of the reflexivity judgement apparatus 500 will be described in accordance with FIG. 13.

[Presentation Unit 510]

In S510, the presentation unit 510 presents the subject with the focus point image of task 1A as a visual cue. Alternatively, in S510, the presentation unit 510 presents the subject with the sound of task 2A as an auditory cue. It is assumed that the focus point image/sound is presented in response to an instruction from the control unit 580.

[Control Unit 580]

The control unit 580 controls presentation of the image (sound) by the presentation unit 510, and also implements control for executing task 1A (task 2A) by implementing control so that the eyeball movement acquisition unit 520 acquires information relating to the eyeball movement of the subject while the image (sound) is being presented in the third time interval.

[Eyeball Movement Acquisition Unit 520]

In S520, the eyeball movement acquisition unit 520, in response to an instruction from the control unit 580, acquires and outputs information relating to the eyeball movement performed by the subject during the third time interval. Here, a time series of information indicating the position of the pupil and a time series of information indicating the position of the iris are acquired as the eyeball movement information.

[Feature Value Extraction Unit 530]

In S530, the feature value extraction unit 530 extracts and outputs the feature value of the saccade appearing in the eyeball movement of the subject from the eyeball movement information acquired in S520. More specifically, the feature value extraction unit 530 determines the damping coefficient of the saccade appearing in the pupil from the time series of information indicating the position of the pupil, determines the damping coefficient of the saccade appearing in the iris from the time series of information indicating the position of the iris, and extracts the difference between the damping coefficient of the saccade appearing in the pupil and the damping coefficient of the saccade appearing in the iris as the feature value of the saccade appearing in the eyeball movement. The feature value may be determined using a step response model, in a similar manner to the feature value extraction unit 130.

Note that when the extraction procedure is executed a plurality of times, respective representative values of the extracted values may be set as the feature value. An average value, a median value, a maximum value, a minimum value, or the like may be used as the representative value.

[Judgement Unit 540]

In S540, the judgement unit 540 generates and outputs a judgement result indicating whether or not the eye of the subject is susceptible to reflexes on the basis of the degree of difference between the reference value recorded in the recording unit 190 and the feature value extracted in S530. More specifically, the judgement unit 540 generates a judgement result indicating that the eye of the subject is susceptible to reflexes when the degree of difference is large, and generates a judgement result indicating that the eye of the subject cannot be considered susceptible to reflexes in other cases. This will now be described in detail. When $\alpha$ is set as the feature value, $\alpha_c$ is set as the reference value, and $\Delta$ ($\Delta \geq 0$) is set as a predetermined value, and a difference $\alpha_c - \alpha$ between the reference value and the feature value is either larger than the predetermined value $\Delta$ or no smaller than the predetermined value $\Delta$, a judgement result indicating that the eye of the subject is susceptible to reflexes is generated, and in other cases, a judgement result indicating that the eye of the subject cannot be considered susceptible to reflexes is generated. Note that by setting $\Delta$ at $\Delta > 0$, an error can be permitted when determining the magnitude relationship.

With the embodiment according to the present invention, it is possible to judge the reflexivity of an eyeball movement. More specifically, it is possible to judge whether or not the eye of the subject is susceptible to reflexes.

Sixth Embodiment

Here, an embodiment in which the susceptibility of the eye of the subject to reflexes is judged on the basis of the findings described in the fifth embodiment will be described. In this embodiment, a reflexivity judgement model into which a feature value, learned by a machine learning method, is input as the feature value of the saccade appearing in the eyeball movement, and which outputs information indicating the susceptibility of the eye to reflexes is used.

A reflexivity judgement apparatus 600 generates information indicating the susceptibility of the eye of the subject to reflexes.

The reflexivity judgement apparatus 600 will be described below with reference to FIGS. 12 and 13. FIG. 12 is a block diagram showing the configuration of the reflexivity judgement apparatus 600. FIG. 13 is a flowchart showing an operation of the reflexivity judgement apparatus 600. As shown in FIG. 12, the reflexivity judgement apparatus 600 includes the presentation unit 510, the eyeball movement acquisition unit 520, the feature value extraction unit 530, a judgement unit 640, the control unit 580, and the recording unit 190. The recording unit 190 is a constituent part that records information required during processing executed by the reflexivity judgement apparatus 600 as appropriate. For example, a reflexivity judgement model is recorded in the recording unit 190 in advance. Here, the reflexivity judgement model is a learned model learned by a machine learning method to output information indicating the susceptibility of the eye to reflexes using a feature value of a saccade appearing in an eyeball movement as input. The input feature value is the difference between the damping coefficient of the saccade appearing in the pupil movement and the damping coefficient of the saccade appearing in the iris movement. Further, the information indicating the susceptibility to reflexes indicates a rank of the susceptibility to reflexes. For example, a hierarchy of three ranks, namely A, B, and C, may be set, and the susceptibility to reflexes may be indicated in order from A. In this case, A indicates the highest susceptibility to reflexes, and C indicates the lowest susceptibility to reflexes.

A method for learning the reflexivity judgement model will be described below.

An operation of the reflexivity judgement apparatus 600 will be described in accordance with FIG. 13.

[Judgement Unit 640]

In S640, the judgement unit 640 uses the reflexivity judgement model recorded in the recording unit 190 to generate and output, as a judgement result, information indicating the susceptibility of the eye of the subject to reflexes from the feature value of the saccade appearing in the eyeball movement of the subject (in other words, the difference between the damping coefficient of the saccade appearing in the pupil movement and the damping coefficient of the saccade appearing in the iris movement) extracted in S530.

With the embodiment according to the present invention, it is possible to judge the reflexivity of an eyeball movement. More specifically, it is possible to judge the susceptibility of the eye of the subject to reflexes.

Seventh Embodiment

A reflexivity judgement model learning apparatus 700 learns the reflexivity judgement model used by the reflexivity judgement apparatus 600.

Figure 14:
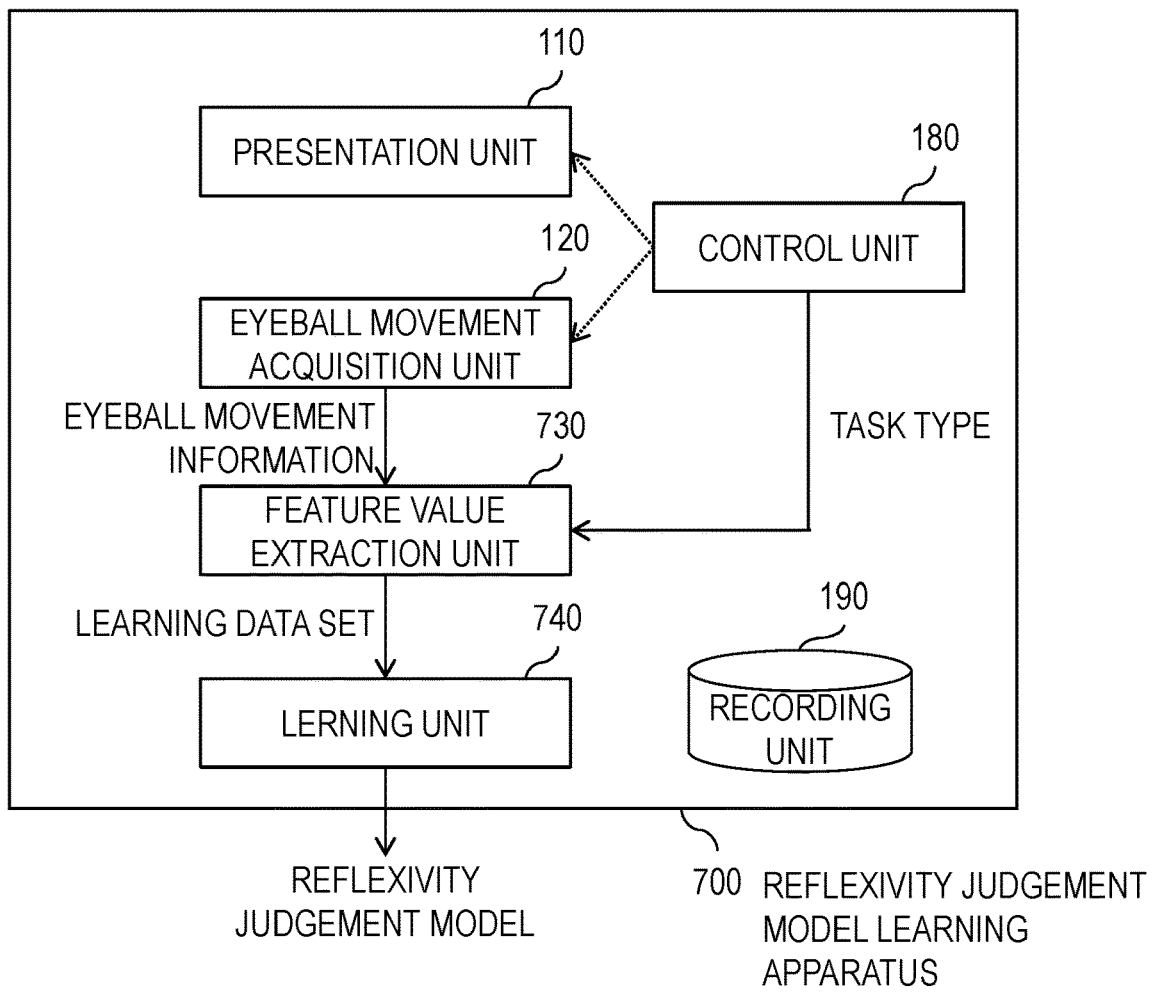
FIG. 14 is a block diagram showing an example configuration of a reflexivity judgement model learning apparatus 700.
Figure 15:
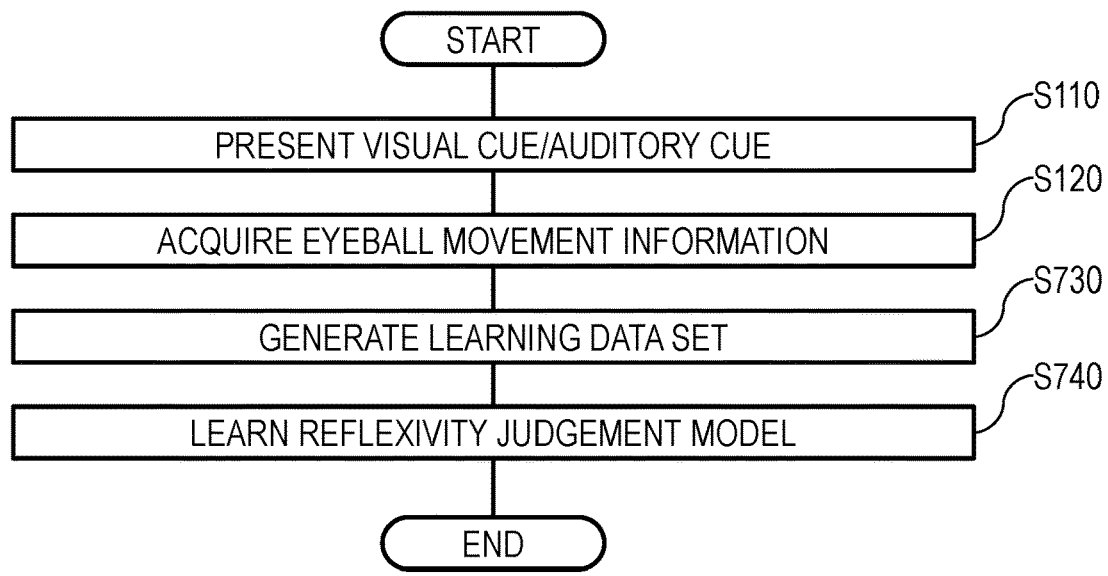
FIG. 15 is a flowchart showing an example operation of the reflexivity judgement model learning apparatus 700.

The reflexivity judgement model learning apparatus 700 will be described below with reference to FIGS. 14 and 15. FIG. 14 is a block diagram showing the configuration of the reflexivity judgement model learning apparatus 700. FIG. 15 is a flowchart showing an operation of the reflexivity judgement model learning apparatus 700. As shown in FIG. 14, the reflexivity judgement model learning apparatus 700 includes the presentation unit 110, the eyeball movement acquisition unit 120, a feature value extraction unit 730, a learning unit 740, the control unit 180, and the recording unit 190. The recording unit 190 is a constituent part that records information required during processing executed by the reflexivity judgement model learning apparatus 700 as appropriate.

An operation of the reflexivity judgement model learning apparatus 700 will be described in accordance with FIG. 14.

[Eyeball Movement Acquisition Unit 120]

In S120, the eyeball movement acquisition unit 120, in response to an instruction from the control unit 180, acquires and outputs information relating to the eyeball movement performed by the subject during the third time interval. Here, a time series of information indicating the position of the pupil and a time series of information indicating the position of the iris are acquired as the eyeball movement information.

[Feature Value Extraction Unit 730]

In S730, the feature value extraction unit 730 extracts the feature value of the saccade appearing in the eyeball movement of the subject from eyeball movement information acquired when the subject executes task 1A (task 2A) using the eyeball movement information acquired in S120 and the task type, which is input from the control unit 180, as input, calculates information indicating the susceptibility of the eye of the subject to reflexes on the basis of the error rate, i.e. the ratio of the number of times the subject executes task 1B (task 2B) erroneously by orienting the eyes in a forward direction (the movement direction of the focus point) to the total number of times the subject executes the task, and then generates and outputs a group including the feature value and the information indicating the susceptibility of the eye to reflexes as learning data. The feature value extracted here is identical to the feature value serving as the input of the reflexivity judgement model, i.e. the difference between the damping coefficient of the saccade appearing in the pupil and the damping coefficient of the saccade appearing in the iris. Note that the information indicating the susceptibility of the eye to reflexes, which serves as an element of the learning data, corresponds to a correct answer label. The generated learning data are recorded in the recording unit 190.

Note that the error rate itself may be used as the information indicating the susceptibility of the eye to reflexes. In this case, a higher error rate indicates a higher susceptibility to reflexes. Further, the range of the error rate may be divided into a plurality of sections, a label denoting a rank may be applied to each section, and the rank may be used as the information indicating the susceptibility to reflexes. For example, when labels A, B, and C are applied in order from the section with the highest error rate, A serves as information indicating the highest susceptibility to reflexes, and C serves as information indicating the lowest susceptibility to reflexes.

A set of the learning data generated in S730 will be referred to as a learning data set. The learning data set is generated by having the control unit 180 execute task 1A or task 2A (the pro-saccade task) and task 1B or task 2B (the anti-saccade task) a plurality of times each on a plurality of subjects.

[Learning Unit 740]

In S740, the learning unit 740 learns the reflexivity judgement model using the learning data set constituted by a set of the learning data generated in S730.

Similarly to the learning unit 440, a support vector machine (SVM) or a neural network, for example, can be used to learn the reflexivity judgement model.

With the embodiment according to the present invention, it is possible to learn a reflexivity judgement model used to judge the reflexivity of an eyeball movement.

Eighth Embodiment

When the eye of the subject is in a state of being likely to move reflexively, the subject is thought to be more likely to focus on external factors. Hence, using the reflexivity judgement apparatus 200/300, it is possible to judge whether or not the subject is likely to focus on external factors. For example, in the case of a task in which it is more appropriate not to focus on external factors, such as a task requiring concentration, a judgement can be made as to whether or not the subject is currently in a suitable state to perform the task. Conversely, in the case of a movement or a task in which it is more appropriate to focus on external factors, a judgement can be made as to whether or not the subject is currently in a suitable state to perform the movement/task.

To be able to judge whether or not the subject is likely to focus on external factors, the judgement unit 240/340 may generate a judgement result indicating whether or not the subject is likely to focus on external factors instead of generating a judgement result indicating whether or not the eye of the subject is likely to move reflexively.

<Additional Remarks>

The apparatus of the present invention includes, as a single hardware entity, for example, an input unit to which a keyboard or the like can be connected, an output unit to which a liquid crystal display or the like can be connected, a communication unit to which a communication device (a communication cable, for example) capable of communicating with the exterior of the hardware entity can be connected, a CPU (Central Processing Unit, which may also include a cache memory, a register, and so on), a RAM and a ROM serving as memory, an external storage device constituted by a hard disk, and a bus that connects the input unit, the output unit, the communication unit, the CPU, the RAM, the ROM, and the external storage device so that data can be exchanged therebetween. If necessary, the hardware entity may also be provided with a device (a drive) capable of performing reading/writing operations with respect to a recording medium such as a CD-ROM, and so on. A general-purpose computer or the like may be used as a physical entity including these hardware resources.

The external storage device of the hardware entity stores a program required to realize the functions described above, data required during the processing of the program, and so on (the program may be stored on a ROM serving as a read-only storage device, for example, instead of the external storage device). Further, data and the like acquired as a result of the processing of the programs are stored as appropriate in the RAM, the external storage device, or the like.

In the hardware entity, the programs stored in the external storage device (or the ROM or the like) and the data required during the processing of the programs are read to the memory as required and interpreted/processed by the CPU as appropriate. As a result, the CPU realizes predetermined functions (the respective constituent requirements expressed above as units, means, or the like).

The present invention is not limited to the embodiments described above and may be modified as appropriate within a scope that does not depart from the spirit of the invention. Moreover, the processing described in the embodiments is not limited to being executed in chronological order, as described above, and depending on the processing power of the device that executes the processing or as necessary, the processing may also be executed in parallel or individually.

When the processing functions of the hardware entity (the apparatus of the present invention) described in the above embodiments are realized by a computer, as described above, the processing content of the functions to be exhibited by the hardware entity is described by a program. By having the computer execute this program, the processing functions of the hardware entity described above are realized on the computer.

The program describing the processing content can be recorded in advance on a computer-readable recording medium. A component such as a magnetic recording device, an optical disk, a magneto-optical recording medium, or a semiconductor memory, for example, may be used as desired as the computer-readable recording medium. More specifically, for example, a hard disk device, a flexible disk, magnetic tape, or the like may be used as the magnetic recording device, a DVD (Digital Versatile Disc), a DVD-RAM (Random Access Memory), a CD-ROM (Compact Disc Read Only Memory), a CD-R (Recordable)/RW (Rewritable), or the like may be used as the optical disk, an MO (Magneto-Optical disc) or the like may be used as the magneto-optical recording medium, and an EEP-ROM (Electronically Erasable and Programmable-Read Only Memory) or the like may be used as the semiconductor memory.

Furthermore, the program is distributed by, for example, selling, transferring, or lending a portable recording medium, such as a DVD or a CD-ROM, on which the program is recorded, or the like. Moreover, the program may be stored in a storage device of a server computer, and the program may be distributed by transferring the program from the server computer to another computer over a network.

For example, the computer that executes the program first stores the program recorded on the portable recording medium or the program transferred from the server computer temporarily in a storage device provided therein. Then, when the processing is to be executed, the computer reads the program stored on a storage device provided therein and executes processing in accordance with the read program. Further, as other embodiments of the program, the computer may read the program directly from the portable recording medium and execute processing in accordance with the program, or the computer may execute processing in accordance with the program received from the server computer successively every time the program is transferred to the computer from the server computer. Moreover, the processing described above may be executed using a so-called ASP (Application Service Provider) system in which, instead of transferring the program to the computer, the processing functions are realized only by instructing execution thereof and acquiring results. Note that the program according to this embodiment is assumed to include information that is used in processing performed by an electronic computer and is equivalent to a program (such as data that do not constitute a direct command issued to the computer but have a property of defining the processing of the computer).

Furthermore, although in this embodiment, a hardware entity is configured by executing a predetermined program on a computer, at least a part of the processing content may be realized in the form of hardware.

The invention claimed is:

1. A reflexivity judgement apparatus comprising:
a feature value extraction circuitry that extracts a feature value of a saccade appearing in an eyeball movement performed by a subject; and
a judgement circuitry that generates a judgement result indicating whether or not an eye of the subject is likely to move reflexively on the basis of a degree of difference between the feature value and a reference feature value of a saccade appearing in an eyeball movement performed by the subject in a state of concentration, wherein
in a case where the feature value of the saccade appearing in the eyeball movement is a difference between a damping coefficient of a saccade appearing in a pupil movement and a damping coefficient of a saccade appearing in an iris movement,
the judgement circuitry generates a judgement result indicating that the eye of the subject is likely to move reflexively when a difference between the reference feature value and the feature value is either larger than a predetermined value or no smaller than the predetermined value and generates a judgement result indicating that the eye of the subject cannot be considered likely to move reflexively when the difference between the reference feature value and the feature value is either no larger than a predetermined value or smaller than the predetermined value, and
in a case where the feature value of the saccade appearing in the eyeball movement is a difference between a damping ratio of the saccade appearing in the pupil movement and a damping ratio of the saccade appearing in the iris movement,
the judgement circuit generates a judgement result indicating that the eye of the subject is likely to move reflexively when a difference between the feature value and the reference feature value is either larger than a predetermined value or no smaller than the predetermined value and generates a judgement result indicating that the eye of the subject cannot be considered likely to move reflexively when the difference between the feature value and the reference feature value is either no larger than a predetermined value or smaller than the predetermined value.

2. A non-transitory computer-readable storage medium which stores a program for causing a computer to function as the reflexivity judgement apparatus according to claim 1.

3. A reflexivity judgement apparatus comprising:
a feature value extraction circuitry that extracts a feature value of a saccade appearing in an eyeball movement performed by a subject; and
a judgement circuitry that generates a judgement result indicating whether or not an eye of the subject is likely to move reflexively from the feature value of the saccade appearing in the eyeball movement using a reflexivity judgement model that has been learned to output a judgement result indicating whether or not the eye is likely to move reflexively in response to input of a feature value of a saccade appearing in an eyeball movement,
wherein the feature value of the saccade appearing in the eyeball movement includes at least one of a difference between a damping coefficient of a saccade appearing in a pupil movement and a damping coefficient of a saccade appearing in an iris movement, and a difference between a damping ratio of the saccade appearing in the pupil movement and a damping ratio of the saccade appearing in the iris movement.

4. A non-transitory computer-readable storage medium which stores a program for causing a computer to function as the reflexivity judgement apparatus according to claim 3.

5. A reflexivity judgement apparatus comprising:
a feature value extraction circuitry that extracts a feature value of a saccade appearing in an eyeball movement performed by a subject; and
a judgement circuitry that generates a judgement result indicating whether or not an eye of the subject is susceptible to reflexes on the basis of a degree of difference between the feature value and a reference feature value of saccades appearing in eyeball movements acquired by having a plurality of subjects execute a task involving moving the eye so as to follow a visual cue or an auditory cue,
wherein the judgement circuitry generates a judgement result indicating that the eye of the subject is susceptible to reflexes when a difference between the reference feature value and the feature value is either larger than a predetermined value or no smaller than the predetermined value and generates a judgement result indicating that the eye of the subject cannot be considered susceptible to reflexes when the difference between the reference feature value and the feature value is either no larger than a predetermined value or smaller than the predetermined value,
the feature value of the saccade appearing in the eyeball movement is a difference between a damping coefficient of a saccade appearing in a pupil movement and a damping coefficient of a saccade appearing in an iris movement, and the reference feature value is either an average value, a median value, a maximum value, or a minimum value of the difference between the damping coefficient of the saccade appearing in the pupil movement and the damping coefficient of the saccade appearing in the iris movement, acquired by having the plurality of subjects execute the task.

6. A non-transitory computer-readable storage medium which stores a program for causing a computer to function as the reflexivity judgement apparatus according to claim 5.

7. A reflexivity judgement apparatus comprising:
a feature value extraction circuitry that extracts a feature value of a saccade appearing in an eyeball movement performed by a subject; and
a judgement circuitry that generates, as a judgement result, information indicating a degree of susceptibility of an eye of the subject to reflexes from the feature value of the saccade appearing in the eyeball movement using a reflexivity judgement model that has been learned to output information indicating the degree of susceptibility of the eye to reflexes in response to input of a feature value of a saccade appearing in an eyeball movement,
wherein the feature value of the saccade appearing in the eyeball movement is a difference between a damping coefficient of a saccade appearing in a pupil movement and a damping coefficient of a saccade appearing in an iris movement.

8. A non-transitory computer-readable storage medium which stores a program for causing a computer to function as the reflexivity judgement apparatus according to claim 7.

9. A reflexivity judgement method comprising:
extracting, via the reflexivity judgement apparatus, a feature value of a saccade appearing in an eyeball movement performed by a subject; and
generating, via the reflexivity judgement apparatus, a judgement result indicating whether or not an eye of the subject is likely to move reflexively on the basis of a degree of difference between the feature value and a reference feature value of a saccade appearing in an eyeball movement performed by the subject in a state of concentration,
wherein, in a case where the feature value of the saccade appearing in the eyeball movement is a difference between a damping coefficient of a saccade appearing in a pupil movement and a damping coefficient of a saccade appearing in an iris movement, a judgement result indicating that the eye of the subject is likely to move reflexively is generated when a difference between the reference feature value and the feature value is either larger than a predetermined value or no smaller than the predetermined value and a judgement result indicating that the eye of the subject cannot be considered likely to move reflexively is generated when the difference between the reference feature value and the feature value is either no larger than a predetermined value or smaller than the predetermined value, and in a case where the feature value of the saccade appearing in the eyeball movement is a difference between a damping ratio of the saccade appearing in the pupil movement and a damping ratio of the saccade appearing in the iris movement, a judgement result indicating that the eye of the subject is likely to move reflexively is generated when a difference between the feature value and the reference feature value is either larger than a predetermined value or no smaller than the predetermined value and a judgement result indicating that the eye of the subject cannot be considered likely to move reflexively is generated when the difference between the feature value and the reference feature value is either no larger than a predetermined value or smaller than the predetermined value.

10. A reflexivity judgement method comprising:
extracting, via a reflexivity judgement apparatus, a feature value of a saccade appearing in an eyeball movement performed by a subject; and
generating, via the reflexivity judgement apparatus, a judgement result indicating whether or not an eye of the subject is likely to move reflexively from the feature value of the saccade appearing in the eyeball movement using a reflexivity judgement model that has been learned to output a judgement result indicating whether or not the eye is likely to move reflexively in response to input of a feature value of a saccade appearing in an eyeball movement,
wherein the feature value of the saccade appearing in the eyeball movement includes at least one of a difference between a damping coefficient of a saccade appearing in a pupil movement and a damping coefficient of a saccade appearing in an iris movement, and a difference between a damping ratio of the saccade appearing in the pupil movement and a damping ratio of the saccade appearing in the iris movement.

11. A reflexivity judgement method comprising:
extracting, via a reflexivity judgement apparatus, a feature value of a saccade appearing in an eyeball movement performed by a subject; and
generating, via the reflexivity judgement apparatus, a judgement result indicating whether or not an eye of the subject is susceptible to reflexes on the basis of a degree of difference between the feature value and a reference feature value of saccades appearing in eyeball movements acquired by having a plurality of subjects execute a task involving moving the eye so as to follow a visual cue or an auditory cue,
wherein a judgement result indicating that the eye of the subject is susceptible to reflexes is generated when a difference between the reference feature value and the feature value is either larger than a predetermined value or no smaller than the predetermined value and a judgement result indicating that the eye of the subject cannot be considered susceptible to reflexes is generated when the difference between the reference feature value and the feature value is either no larger than a predetermined value or smaller than the predetermined value,
the feature value of the saccade appearing in the eyeball movement is a difference between a damping coefficient of a saccade appearing in a pupil movement and a damping coefficient of a saccade appearing in an iris movement, and
the reference feature value is either an average value, a median value, a maximum value, or a minimum value of the difference between the damping coefficient of the saccade appearing in the pupil movement and the damping coefficient of the saccade appearing in the iris movement, acquired by having the plurality of subjects execute the task.

12. A reflexivity judgement method comprising:
extracting, via a reflexivity judgement apparatus, a feature value of a saccade appearing in an eyeball movement performed by a subject; and
generating, via the reflexivity judgement apparatus, as a judgement result, information indicating a degree of susceptibility of an eye of the subject to reflexes from the feature value of the saccade appearing in the eyeball movement using a reflexivity judgement model that has been learned to output information indicating the degree of susceptibility of the eye to reflexes in response to input of a feature value of a saccade appearing in an eyeball movement,
wherein the feature value of the saccade appearing in the eyeball movement is a difference between a damping coefficient of a saccade appearing in a pupil movement and a damping coefficient of a saccade appearing in an iris movement.

\* \* \* \* \*